US008530668B2

(12) United States Patent
Takayama et al.

(10) Patent No.: US 8,530,668 B2
(45) Date of Patent: Sep. 10, 2013

(54) PHARMACEUTICAL COMPOSITION CONTAINING OPTICALLY ACTIVE COMPOUND HAVING THROMBOPOIETIN RECEPTOR AGONIST ACTIVITY, AND INTERMEDIATE THEREFOR

(75) Inventors: Masami Takayama, Osaka (JP); Noriyuki Kurose, Osaka (JP)

(73) Assignee: Shionogi & Co., Ltd., Osaki-Shi, Osaka (JP)

( * ) Notice: Subject to any disclaimer, the term of this patent is extended or adjusted under 35 U.S.C. 154(b) by 396 days.

(21) Appl. No.: 12/671,476

(22) PCT Filed: Jul. 29, 2008

(86) PCT No.: PCT/JP2008/063541
§ 371 (c)(1),
(2), (4) Date: Jun. 24, 2010

(87) PCT Pub. No.: WO2009/017098
PCT Pub. Date: Feb. 5, 2009

(65) Prior Publication Data
US 2010/0267783 A1 Oct. 21, 2010

(30) Foreign Application Priority Data
Jul. 31, 2007 (JP) ................................. 2007-198590

(51) Int. Cl.
*C07D 277/38* (2006.01)
*A61K 31/425* (2006.01)

(52) U.S. Cl.
USPC .......................................... 548/190; 514/371

(58) Field of Classification Search
None
See application file for complete search history.

(56) References Cited

U.S. PATENT DOCUMENTS

| 7,601,746 | B2 * | 10/2009 | Takayama et al. | 514/370 |
| 2007/0043087 | A1 * | 2/2007 | Takayama et al. | 514/342 |
| 2009/0318513 | A1 * | 12/2009 | Takayama et al. | 514/366 |
| 2010/0022542 | A1 * | 1/2010 | Takemoto et al. | 514/236.8 |

FOREIGN PATENT DOCUMENTS

| EP | 1 207 155 A1 | 5/2002 |
| EP | 1 253 142 A1 | 10/2002 |
| EP | 1 354 880 A1 | 10/2003 |
| EP | 1 357 116 A1 | 10/2003 |
| EP | 1 361 220 A1 | 11/2003 |
| EP | 1 466 912 A1 | 10/2004 |
| EP | 1 647 553 A1 | 4/2006 |
| EP | 1 655 291 A1 | 5/2006 |
| JP | 10-72492 | 3/1998 |
| JP | 10-287634 | 10/1998 |
| JP | 11-1477 | 1/1999 |
| JP | 11-152276 | 6/1999 |
| JP | 2006-219480 | 8/2006 |
| JP | 2006-219481 | 8/2006 |
| WO | WO 96/40750 | 12/1996 |
| WO | WO 00/35446 | 6/2000 |
| WO | WO 2004/029049 A1 | 4/2004 |
| WO | WO 2005014561 A1 * | 2/2005 |
| WO | WO 2007/004038 A1 | 1/2007 |
| WO | WO 2007/036709 A2 | 4/2007 |
| WO | WO 2007/054783 A2 | 5/2007 |

OTHER PUBLICATIONS

Nogami et al. Haematologica (2008), 93(10), 1495-1504.*
International Search Report from the Japanese Patent Office for International Application No. PCT/JP2008/063541, mailed Sep. 22, 2008.
Vigon, I. et al., "Molecular Cloning and Characterization of *MPL*, the Human Homolog of the *v-mpl*Oncogene: Identification of a Member of the Hematopoietic Growth Factor Receptor Superfamily," Pro. Natl. Acad. Sci., vol. 89, pp. 5640-5644, (Jun. 1992).
Collins, M. K. L. et al., "Transfer of Functional EGF Receptors to an IL3-Dependent Cell Line," Journal of Cellular Physiology, vol. 137, pp. 293-298, (1988).

* cited by examiner

*Primary Examiner* — Nyeemah A Grazier
(74) *Attorney, Agent, or Firm* — Finnegan, Henderson, Farabow, Garrett & Dunner LLP

(57) ABSTRACT

An optically active 4-phenylthiazole derivative having a thrombopoietin receptor agonist activity and a pharmaceutical composition containing the present compound as an active ingredient are created, and a platelet production regulating agent which can be orally administered is provided.
Disclosed is a pharmaceutical composition containing, as an active ingredient, an optically active compound represented by the formula:

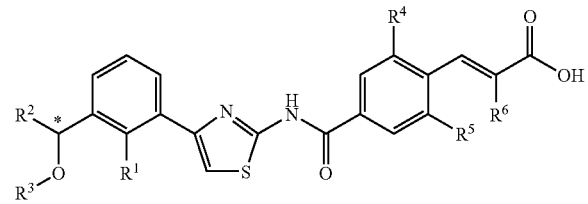

wherein, $R^1$ is a halogen atom or C1-C3 alkyloxy; $R^2$ is C1-C8 alkyl; $R^3$ is C1-C8 alkyl; $R^4$ and $R^5$ are each independently a fluorine atom or chlorine atom; $R^6$ is C1-C3 alkyl or C1-C3 alkyloxy; * indicates that a carbon atom marked with an asterisk is an asymmetric carbon,
a pharmaceutically acceptable salt thereof, or a solvate thereof.

4 Claims, 6 Drawing Sheets

PHARMACEUTICAL COMPOSITION CONTAINING OPTICALLY ACTIVE COMPOUND HAVING THROMBOPOIETIN RECEPTOR AGONIST ACTIVITY, AND INTERMEDIATE THEREFOR

TECHNICAL FIELD

The present invention relates to a pharmaceutical composition containing, as an active ingredient, an optically active 4-phenylthiazole derivative having a thrombopoietin receptor agonist activity.

BACKGROUND ART

Since thrombopoietin is a polypeptide cytokine consisting of 332 amino acids and it promotes platelet production by stimulating differentiation and proliferation of a megakaryocyte via a receptor, it is expected as an agent for morbidity of a blood disease accompanied with abnormality of the platelet number such as thrombocytopenia. A nucleotide sequence of a gene encoding a thrombopoietin receptor is described in Non-Patent Document 1. In Patent Document 1 and Patent Document 2, low-molecular peptides having affinity for the thrombopoietin receptor are also known, but oral administration of these peptide derivatives are not generally practical.

As a low-molecular compound having affinity for the thrombopoietin receptor, a 1,4-benzothiazepine derivative is described in Patent Document 3 and Patent Document 4, a 1-azonaphthalene derivative is described in Patent Document 5, and a 1,3-thiazole derivative is described in Patent Document 6 to 22.

[Patent Document 1]
  Japanese Patent Application Laid-Open (JP-A) No. 10-72492
[Patent Document 2]
  International Publication WO 96/40750
[Patent Document 3]
  JP-A No. 11-1477
[Patent Document 4]
  JP-A No. 11-152276
[Patent Document 5]
  International Publication WO 00/35446
[Patent Document 6]
  JP-A No. 10-287634
[Patent Document 7]
  International Publication WO 01/07423
[Patent Document 8]
  International Publication WO 01/53267
[Patent Document 9]
  International Publication WO 02/059099
[Patent Document 10]
  International Publication WO 02/059100
[Patent Document 11]
  International Publication WO 02/059100
[Patent Document 12]
  International Publication WO 02/062775
[Patent Document 13]
  International Publication WO 2003/062233
[Patent Document 14]
  International Publication WO 2004/029049
[Patent Document 15]
  International Publication WO 2005/007651
[Patent Document 16]
  International Publication WO 2005/014561
[Patent Document 17]
  JP-A No. 2005-47905
[Patent Document 18]
  JP-A No. 2006-219480
[Patent Document 19]
  JP-A No. 2006-219481
[Patent Document 20]
  International Publication WO 2007/004038
[Patent Document 21]
  International Publication WO 2007/036709
[Patent Document 22]
  International Publication WO 2007/054783
[Non-Patent Document 1]
  Proc. Natl. Acad. Sci. USA, 1992, vol. 89, p. 5640-5644

DISCLOSURE OF THE INVENTION

Problems to be Solved by the Invention

A pharmaceutical composition containing, as an active ingredient, an optically active 4-phenylthiazole derivative having a thrombopoietin receptor agonist activity is created, and a platelet production regulating agent which can be orally administered is provided.

Means to Solve the Problems

In view of the above points, the present inventors have continued to study intensively and, as a result, found out a pharmaceutical composition containing, as an active ingredient, the following optically active 4-phenylthiazole derivative, exhibiting the excellent thrombopoietin receptor agonist activity, and exhibiting the high oral absorbability and/or high in vivo activity, a crystal having high stability and/or high purity, as well as a useful intermediate and a crystal thereof.

That is, the present invention relates to 1) a pharmaceutical composition containing, as an active ingredient, an optically active compound represented by the formula (I):

[Chemical formula 1]

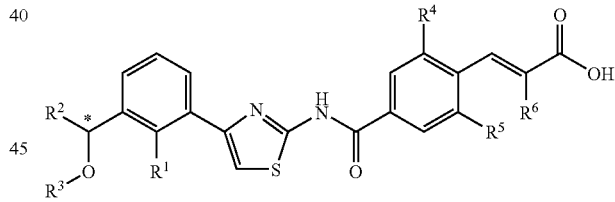

(I)

wherein $R^1$ represents a halogen atom or C1-C3 alkyloxy; $R^2$ represents C1-C8 alkyl; $R^3$ represents C1-C8 alkyl; $R^4$ and $R^5$ each represent independently a fluorine atom or a chlorine atom; $R^6$ represents C1-C3 alkyl or C1-C3 alkyloxy; * indicates that a carbon atom marked with an asterisk is an asymmetric carbon, a pharmaceutically acceptable salt thereof, or a solvate thereof.

The present invention further relates to the following 2) to 23).

2) The pharmaceutical composition according to 1), wherein $R^1$ is methyloxy.
3) The pharmaceutical composition according to 1) or 2), wherein $R^4$ and $R^5$ are both a chlorine atom.
4) The pharmaceutical composition according to any one of 1) to 3), wherein $R^6$ is methyl.
5) The pharmaceutical composition according to 1), wherein $R^1$ is methyloxy, $R^4$ and $R^5$ are both a chlorine atom, and $R^6$ is a methyl.
6) The pharmaceutical composition according to any one of 1) to 5), which is a thrombopoietin receptor agonist.

7) The pharmaceutical composition according to any one of 1) to 5), which is a platelet production regulating agent.

8) Use of an optically active compound represented by the formula (I):

[Chemical formula 2]

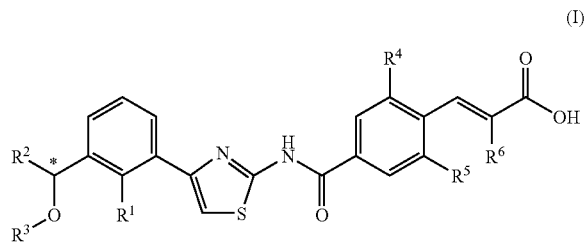

(I)

wherein R¹ represents a halogen atom or C1-C3 alkyloxy; R² represents C1-C8 alkyl; R³ represents C1-C8 alkyl; R⁴ and R⁵ each represent independently a fluorine atom or a chlorine atom; R⁶ represents C1-C3 alkyl or C1-C3 alkyloxy; * indicates that a carbon atom marked with an asterisk is an asymmetric carbon, a pharmaceutically acceptable salt thereof, a solvate thereof for manufacturing a medicament for regulating a platelet production.

9) A method of regulating a platelet production of a mammal, comprising administering an amount exhibiting a therapeutic effect of an optically active compound represented by the formula (I):

[Chemical formula 3]

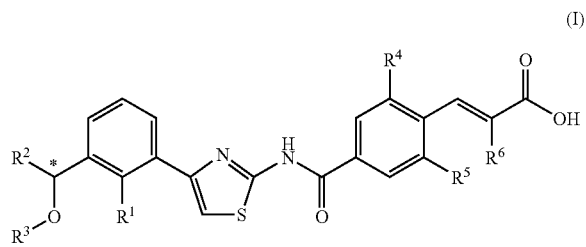

(I)

wherein R¹ represents a halogen atom or C1-C3 alkyloxy; R² represents C1-C8 alkyl; R³ represents C1-C8 alkyl; R⁴ and R⁵ each represent independently a fluorine atom or a chlorine atom; R⁶ represents C1-C3 alkyl or C1-C3 alkyloxy; * indicates that a carbon atom marked with an asterisk is an asymmetric carbon, a pharmaceutically acceptable salt thereof, or a solvate thereof to a mammal including a human.

10) A crystal of (S)-(E)-3-(2,6-dichloro-4-{4-[2-methyloxy-3-(1-methyloxyheptyl)phenyl]thiazol-2-ylcarbamoyl}phenyl)-2-methylacrylic acid having a diffraction angle 2θ of a main peak of powder X-ray diffraction of 4.2, 6.4, 12.3, 13.2, 23.6, 23.8, and 24.7 degrees.

11) A crystal of (S)-(E)-3-(2,6-dichloro-4-{4-[3-(1-hexyloxyethyl)-2-methyloxyphenyl]thiazol-2-ylcarbamoyl}phenyl)-2-methylacrylic acid having a diffraction angle 2θ of a main peak of powder X-ray diffraction of 17.8, 21.1, 22.5, 23.3, 24.1, and 24.4 degrees.

12) A crystal of (S)-(E)-3-(2,6-dichloro-4-{4-[3-(2,2-dimethyl-1-propyloxypropyl)-2-methyloxyphenyl]thiazol-2-ylcarbamoyl}phenyl)-2-methylacrylic acid having a diffraction angle 2θ of a main peak of powder X-ray diffraction of 13.6, 16.1, 21.2, 23.4 and 24.5 degrees.

13) A pharmaceutical composition containing, as an active ingredient, the crystal of the optically active compound as defined in any one of 10) to 12), the crystal of a pharmaceutically acceptable salt thereof, or the crystal of a solvate thereof.

14) The pharmaceutical composition according to 13), which is a thrombopoietin receptor agonist.

15) The pharmaceutical composition according to 14), which is a platelet production regulating agent.

16) Use of the crystal as defined in any one of 10) to 12) for manufacturing a medicament for regulating a platelet production.

17) A method of regulating a platelet production of a mammal, comprising administering an amount exhibiting a therapeutic effect of the crystal as defined in any one of 10) to 12) to a mammal including a human.

18) A crystal of (S)-4-[2-methyloxy-3-(1-methyloxyheptyl)phenyl]thiazol-2-yl amine having a diffraction angle 2θ of a main peak of powder X-ray diffraction of 10.3, 17.7, 18.2, 18.5 and 23.1 degrees.

19) A crystal of (S)-(–)-4-[3-(1-hexyloxyethyl)-2-methyloxyphenyl]thiazol-2-yl amine having a diffraction angle 2θ of a main peak of powder X-ray diffraction of 12.5, 13.0, 13.6, 16.4, 23.0 and 24.3 degrees.

20) A crystal of ethyl 3-(4-carboxy-2,6-dichlorophenyl)-2-methyl methacrylate having a diffraction angle 2θ of a main peak of powder X-ray diffraction of 8.1, 16.3, 19.2, 20.0, 24.8 and 39.0 degrees.

21) An optically active compound represented by the formula (I), a pharmaceutically acceptable salt thereof, or a solvate thereof as a platelet production regulating agent.

22) An optically active compound represented by the formula (I), a pharmaceutically acceptable salt thereof, or a solvate for regulating a platelet production.

23) The optically active compound according to 21) or 22), a pharmaceutically acceptable salt thereof, or a solvate thereof, wherein R¹ is methyloxy.

24) The optically active compound according to 21) or 22), a pharmaceutically acceptable salt thereof, or a solvate thereof, wherein R⁴ and R⁵ are both a chlorine atom.

25) The optically active compound according to any one of 1) to 3), a pharmaceutically acceptable salt thereof, or a solvate thereof, wherein R⁶ is methyl.

26) The optically active compound according to 21), a pharmaceutically acceptable salt thereof, or a solvate thereof, wherein R¹ is methyloxy, R⁴ and R⁵ are both a chlorine atom, and R⁶ is methyl.

The meaning of each term will be explained below. Each term is used as unified meaning herein, and is used in the same meaning when used alone or when used in combination with other terms.

Herein, the "halogen atom" means a fluorine atom, a chlorine atom, a bromine atom, or an iodine atom. A fluorine atom, a chlorine atom, and a bromine atom are preferable.

Herein, the "alkyl" includes a straight or branched monovalent hydrocarbon group of a carbon number of 1 to 8. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl or the like. Preferably, C1-C6 alkyl is exemplified Further, C1-C4 alkyl is preferred. Particularly, when a carbon number is designated, "alkyl" having a carbon number in the number range is meant.

Herein, examples of "alkyloxy" include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy or the like. Preferably, C1-C6 alkyloxy is exemplified. Further, C1-C4 alkyloxy is preferred. Particularly, a carbon number is designated, "alkyloxy" having a carbon number in the number range is meant.

Herein, in the chemical formulas, a carbon atom marked with * means an asymmetric carbon. A compound marked with * means an optical isomer which absolute configuration of a carbon atom marked with * is R configuration or S configuration. For example, an optically active compound represented by the formula (I) includes an optical isomer of R configuration ((R)-I)) or an optical isomer of R configuration ((S)-I)).

[Chemical formula 4]

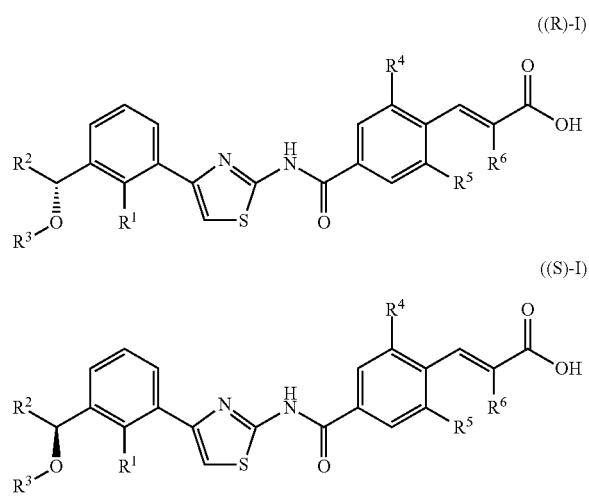

Herein, the "platelet production regulating agent" includes an agent for morbidity of a blood disease accompanied with abnormality of the platelet number such as thrombocytopenia (thrombocytopenia after hematopoietic stem cell transplantation (such as bone marrow transplantation) and the like, thrombocytopenia after chemical therapy, hypoplastic anemia, myelodysplastic syndrome, acquired thrombocytopenia such as idiopathic thrombocytopenic purpura and the like, congenital thrombocytopenia such as thrombopoietin deficiency and the like, virus pneumonia (such as hepatitis C and the like), other hepatic disease (hepatocirrhosis)) and the like. For example, the agent can be used for treating and/or preventing an abnormality of the platelet number due to administration of an anti-cancer agent for hematopoietic organ tumor, solid tumor or the like. When the platelet number is reduced by administration of an anti-cancer agent, the agent can be used as a treating agent and, when reduction in the platelet number due to administration of an anti-cancer agent is expected, the agent can be used as a preventive. When platelet reduction is expected at cardiovascular (such as heart blood vessel) surgical operation, the agent can be used as a therapeutic agent and/or a preventive.

Herein, the "platelet production is regulated" includes 1) increase in the decreased platelet number, 2) maintenance of the platelet number which will be decreased, and 3) reduction in a decreasing degree of the platelet number.

A preferable substituent group of $R^1$ to $R^6$ of the compound represented by the formula (I) is represented by (Ia) to (In). A compound of a possible combination thereof is preferable.

$R^1$ is (Ia) preferably a halogen atom or C1-C3 alkyloxy, (Ib) more preferably a fluorine atom or methyloxy, and (Ic) most preferably methyloxy.

$R^2$ is (Id) preferably C1-C8 alkyl, and (Ie) more preferably C1-C6 alkyl.

$R^3$ is (If) preferably C1-C8 alkyl, and (Ig) more preferably C1-C6 alkyl.

$R^4$ and $R^5$ are both the same, and are (Ih) preferably a fluorine atom or a chlorine atom, and (Ii) more preferably a chlorine atom.

$R^6$ is (Ij) preferably C1-C3 alkyl or C1-C3 alkyloxy, (Ik) more preferably C1-C3 alkyl, and (Il) most preferably methyl.

Optical rotation of an optical isomer is (Im) preferably (+) or (−), and (In) more preferably (−).

In addition, as the optically active compound represented by the formula (I), the following optically active compound is preferable.

[Chemical formula 5]

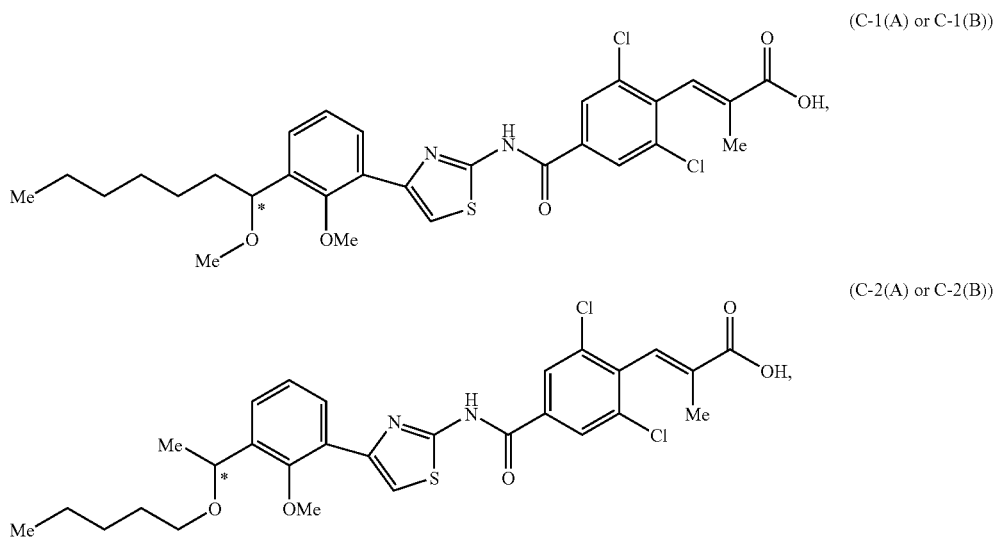

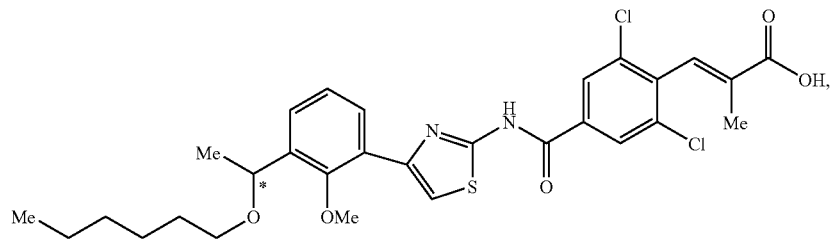
(C-3(A) or C-3(B))
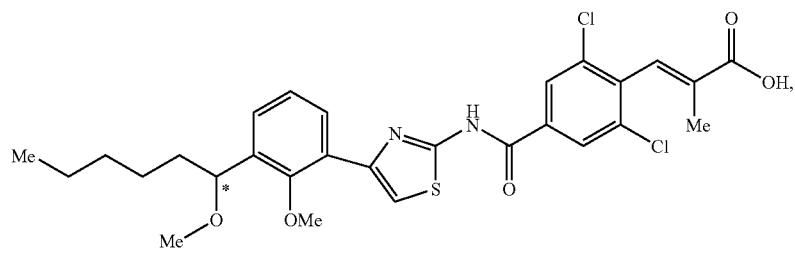
(C-4(A) or C-4(B))
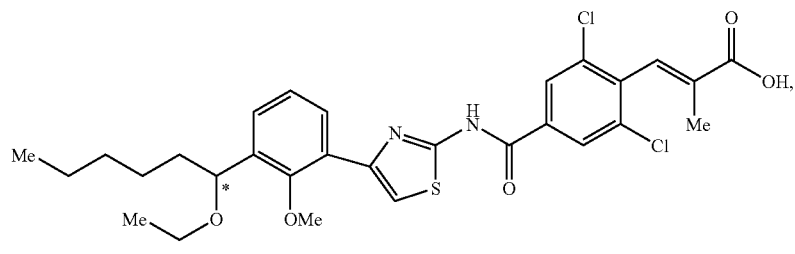
(C-5(A) or C-5(B))
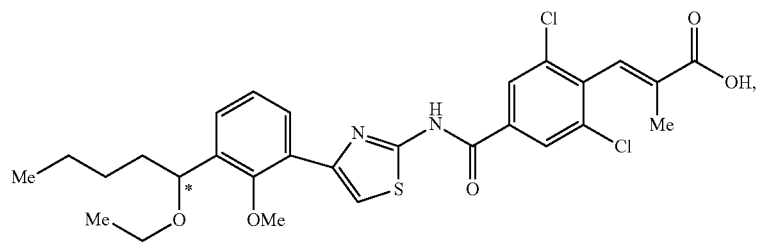
(C-6(A) or C-6(B))
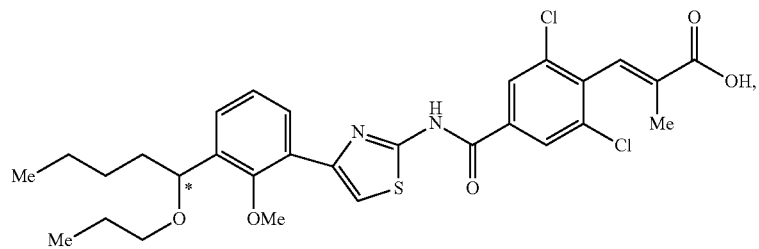
(C-7(A) or C-7(B))
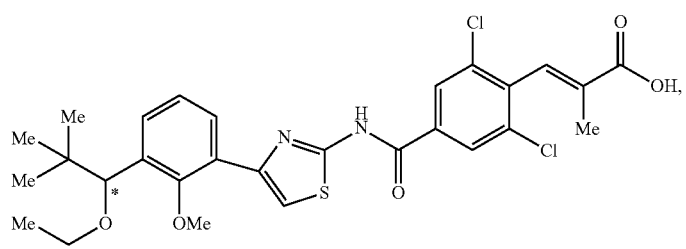
(C-8(A) or C-8(B))

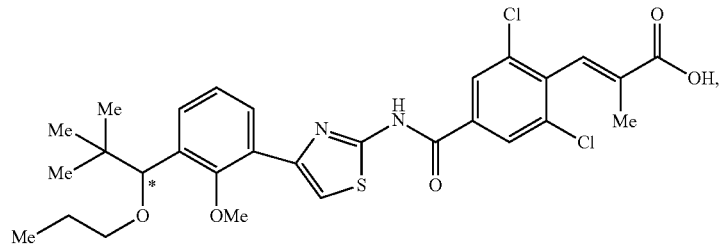
(C-9(A) or C-9(B))
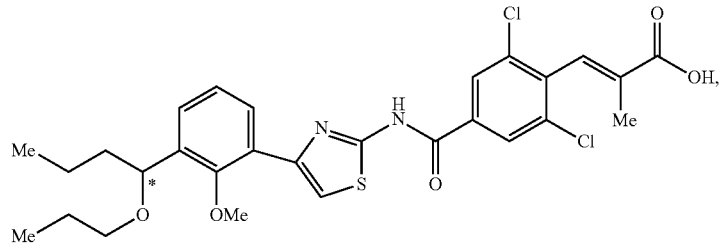
(C-10(A) or C-10(B))
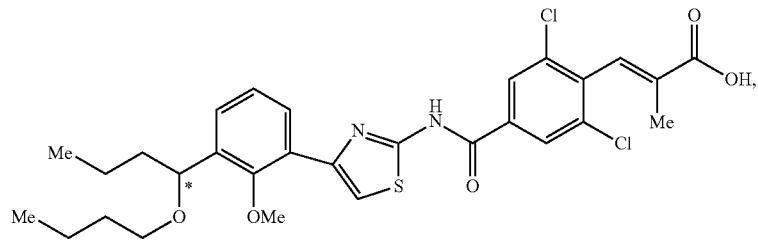
(C-11(A) or C-11(B))
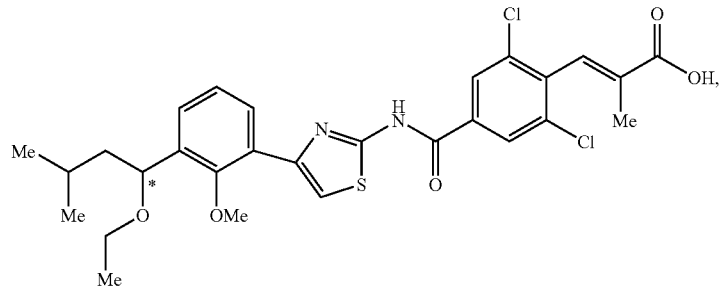
(C-12(A) or C-12(B))
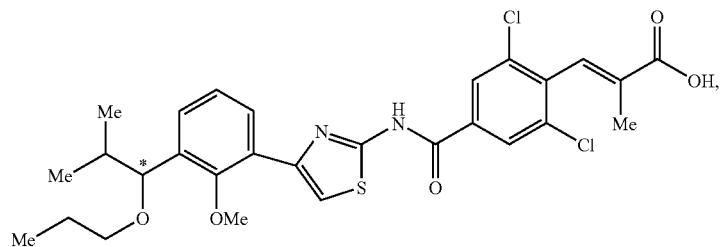
(C-13(A) or C-13(B))
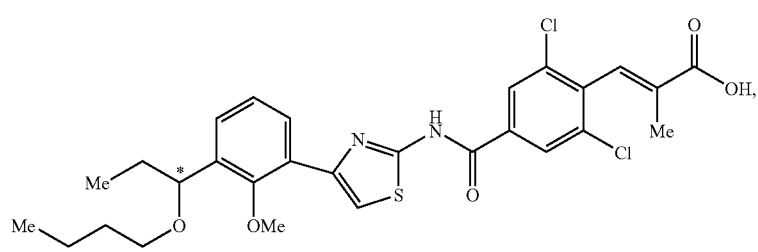
(C-14(A) or C-14(B))

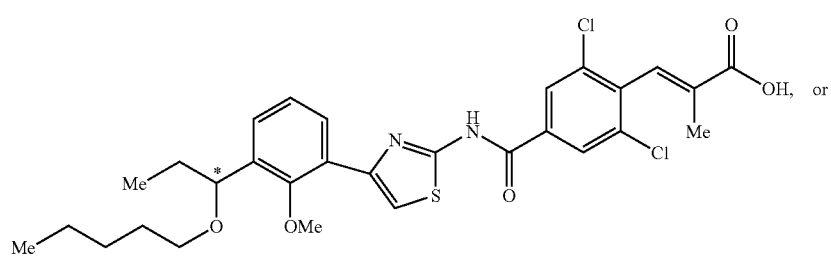

(C-15(A) or C-15(B))

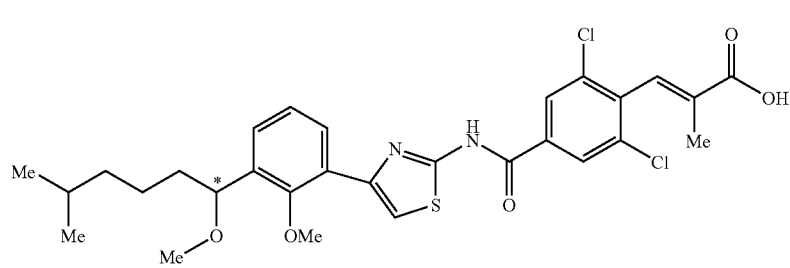

(C-16(A) or C-16(B))

wherein Me represents methyl; * indicates that a carbon atom marked with an asterisk is an asymmetric carbon.

Effect of the Invention

Since an optically active 4-phenylthiazole derivative having a strong thrombopoietin receptor antagonist activity exhibits a high oral absorbability or/and a high in vivo activity, and has a high safety, a pharmaceutical composition containing the optically active 4-phenylthiazole derivative as an active ingredient is useful as, particularly, a platelet production regulating agent. In addition, a crystal has a high stability and/or a high purity, and an intermediate has a high stability, and they are useful in producing a 4-phenylthiazole derivative and/or producing a pharmaceutical composition.

The optically active compound of the formula (I) can be synthesized by the following production methods A to F and the like.

Production Method A

[Chemical formula 6]

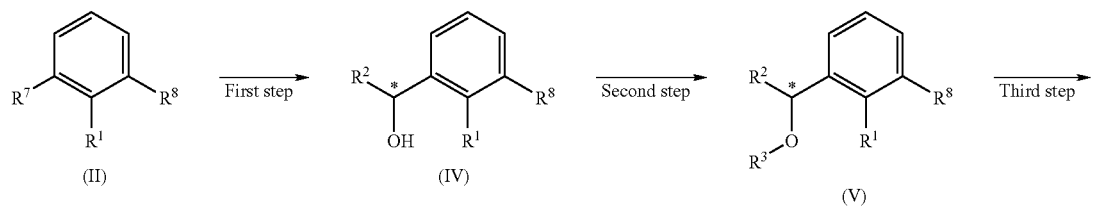

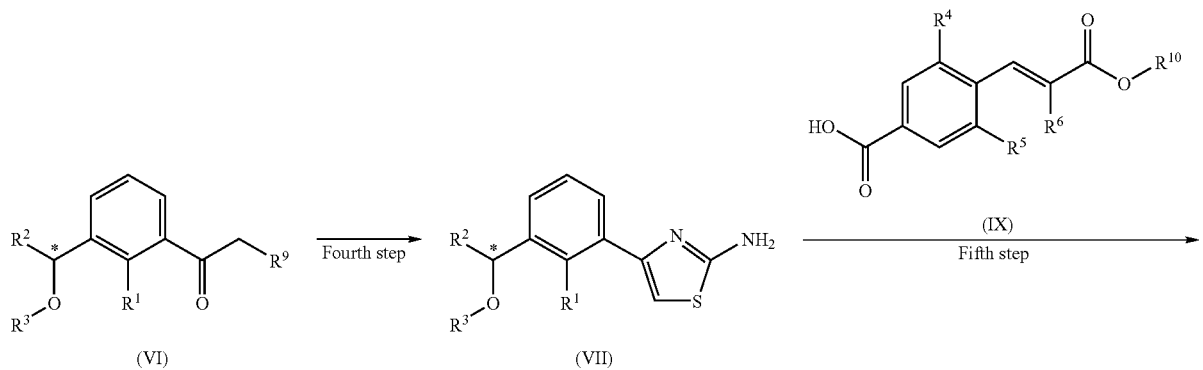

-continued

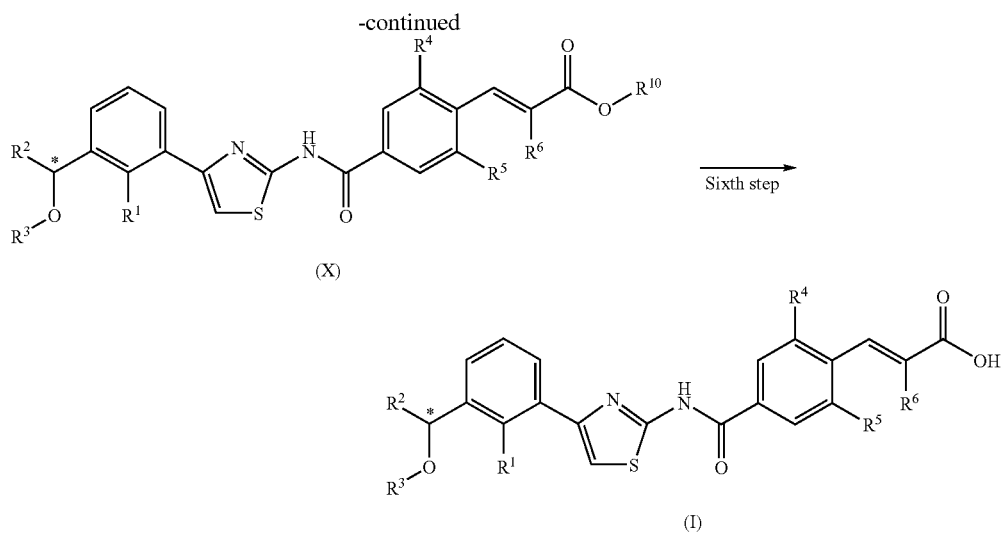

(X)

(I)

wherein $R^1$, $R^2$, $R^3$, $R^4$, $R^5$, and $R^6$ are as defined in 1); $R^7$ and $R^8$ are each independently a chlorine atom, a bromine atom, or an iodine atom; $R^9$ is a fluorine atom, a chlorine atom, or a bromine atom; $R^{10}$ is C1-C6 alkyl.

As a compound represented by the formula (II) as a starting compound, a commercially available product can be used.

A production method A is a method of producing an optically active compound represented by the formula (I) from a compound represented by the formula (II) via the first step to the sixth step.

The first step is a step of treating the compound represented by the formula (II) with magnesium in a solvent to produce a Grignard reagent, and reacting the reagent with a compound represented by the formula: $R^2$CHO (wherein $R^2$ is as defined in 1)) to produce a compound represented by the formula (IV).

Relative to the compound represented by the formula (II), magnesium can be used at 0.5 to 2 mol equivalents, and the compound represented by the formula: $R^2$CHO can be used at 0.5 to 3 mol equivalents.

As the solvent, tetrahydrofuran or the like can be used.

A reaction temperature can be 0° C. to a reflux temperature of a solvent, and a reaction time can be 0.5 to 12 hours.

The second step is a step of alkylating the compound represented by the formula (IV) by using an alkylating agent in the presence of a base to produce a compound represented by the formula (V).

Relative to the compound represented by the formula (IV), the alkylating agent can be used at 0.5 to 2 mol equivalents and, the base can be used at 0.5 to 5 mol equivalents.

As the solvent, N,N-dimethylformamide, tetrahydrofuran and the like can be used alone, or by mixing them.

As the base, sodium hydride, sodium hydroxide, potassium hydroxide, potassium carbonate, cesium carbonate and the like can be used alone, or by mixing them. A reaction temperature can be −10° C. to a reflux temperature of a solvent, and a reaction time can be 0.5 to 12 hours.

The third step is a step of treating the compound represented by the formula (V) with isopropyl magnesium chloride in a solvent to produce a Grignard reagent, and reacting the reagent with a compound represented by the formula: X—C(=O)—CH$_2$—R$^9$ (wherein $R^9$ is as defined above; X is a halogen atom) to produce a compound represented by the formula (VI).

Relative to the compound represented by the formula (V), isopropyl magnesium chloride can be used at 0.5 to 2 mol equivalents, and the compound represented by the formula: $R^9$—CH$_2$—C(=O)—X (wherein $R^9$ and X are as defined above) or the formula: $R^9$—CH$_2$—C(=O)—N(Me)(OMe) (wherein R is as defined above; Me is methyl) can be used at 0.5 to 3 mol equivalents.

As the solvent, tetrahydrofuran or the like can be used.

A reaction temperature can be 0° C. to a reflux temperature of a solvent, and a reaction time can be 0.5 to 12 hours.

The fourth step is a step of reacting the compound represented by the formula (VI) with thiourea in a solvent to produce a compound represented by the formula (VII).

Relative to the compound represented by the formula (VI), thiourea can be used at 0.5 to 2 mol equivalents.

As the solvent, methanol, ethanol, propanol, isopropanol and the like can be used alone, or by mixing them.

A reaction temperature can be 20° C. to a reflux temperature of a solvent, and a reaction time can be 0.5 to 48 hours.

The fifth step is a step of reacting the compound represented by the formula (VII) with a compound represented by the formula (IX) obtained in a production method B to produce a compound represented by the formula (X).

The present step can be conducted by using the same method as the method described in the fourth step of an A method of International Publication WO 2005/014561.

The sixth step is a step of producing a compound represented by the formula (I) by hydrolyzing the compound represented by the formula (X) in a solvent.

The present step can be conducted by using the same method as the method described in the fifth step of an A method of International Publication WO 2005/014561.

The compound obtained in each step can be isolated and purified by a general method such as silica gel column chromatography, recrystallization, and/or distillation. Alternatively, the resulting compound can be also used in a next reaction without purification. When the compound obtained in each step is a racemic compound, an optically active compound is obtained by column chromatography using a chiral column, and each step may be also performed using it.

Production Method B

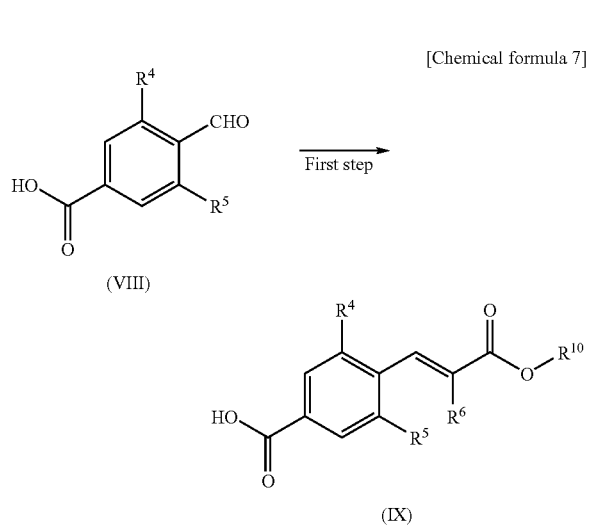

wherein $R^4$, $R^5$ and $R^6$ are as defined in 1); $R^{10}$ is as defined in a production method A. As a compound represented by the formula (VIII) as a starting compound, a commercially available product can be used.

A production method B is a method of producing a compound represented by the formula (IX) from the compound represented by the formula (VIII). The compound represented by the formula (IX) is subjected to the fifth step of a production method A, and is further subjected to the sixth step, thereby, the compound represented by the formula (I) can be produced.

The present step can be conducted by using the same method as the method described in the second step of an A method of International Publication WO 2005/014561.

The compound obtained in each step can be isolated and purified by a general method such as silica gel column chromatography, recrystallization, and/or distillation. Alternatively, the resulting compound can be also used in a next reaction without purification.

Production Method C

[Chemical formula 8]

wherein $R^1$, $R^2$, $R^3$, $R^4$, $R^5$, and $R^6$ are as defined in 1); $R^{10}$ is as defined in a production method A.

As the compound represented by the formula (VII) as a starting compound, the compound produced by a production method A can be used.

A production method C is a method of producing the compound represented by the formula (X) from the compound represented by the formula (VII) via the first step and the second step. The compound represented by the formula (X) can be subjected to the sixth step of a production method A to obtain the compound represented by the formula (I).

In the first step, using the same method as the fifth step of a production method A, the compound represented by the formula (XI) can be obtained by reacting the compound represented by the formula (VII) and the compound represented by the formula (VIII).

In the second step, using the same method as a production method B, the compound represented by the formula (X) can be obtained from a compound represented by the formula (XI).

The compound obtained in each step can be isolated and purified by a general method such as silica gel column chromatography, recrystallization, and/or distillation. Alternatively, the resulting compound can be also used in a next reaction without purification. When the compound obtained in each step is a racemic compound, an optically active compound is obtained by column chromatography using a chiral column, and each step may be also performed using it.

Production Method D

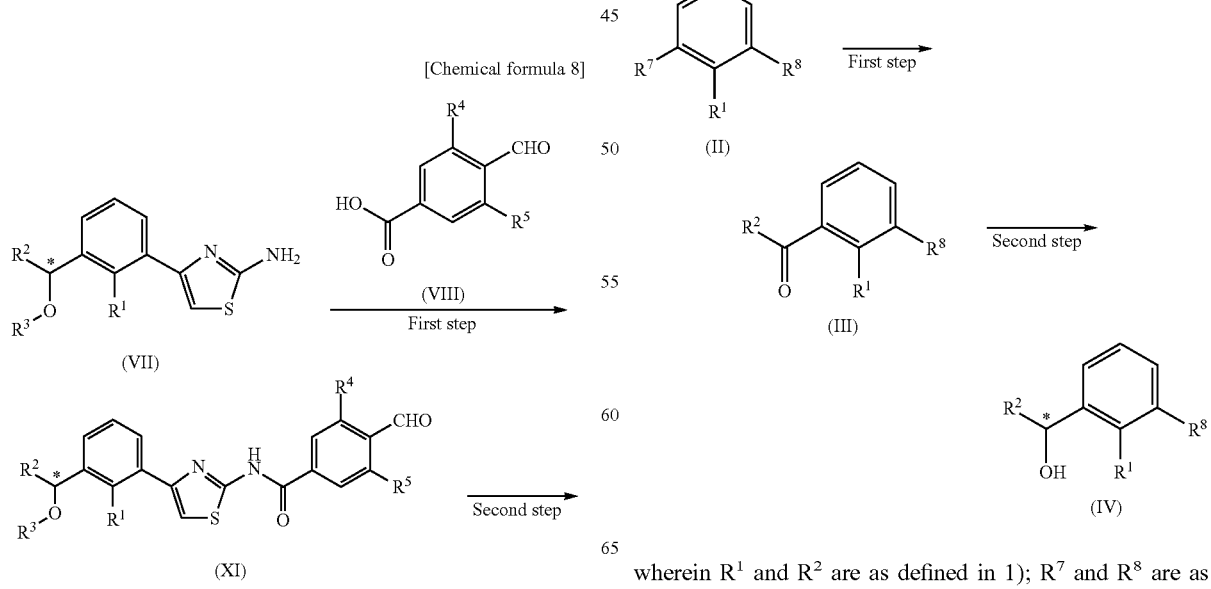

wherein $R^1$ and $R^2$ are as defined in 1); $R^7$ and $R^8$ are as defined in a production method A.

As the compound represented by the formula (II) as a starting compound, a commercially available product can be used.

A production method D is a method of producing the optically active compound represented by the formula (IV) from the compound represented by the formula (II) via the first step and the second step. By subjecting the optically active compound represented by the formula (IV) to the second step to the sixth step of the production method A, the optically active compound represented by the formula (I) can be obtained.

The first step is a step of producing the compound represented by the formula (IV) by treating the compound represented by the formula (II) with magnesium in a solvent to produce a Grignard reagent, and reacting this with a compound represented by the formula: $R^2$—C(=O)—X (wherein $R^2$ is as defined in 1); X is as defined as above) or the formula: $R^2$—C(=O)—N(Me)(OMe) ($R^2$ is as defined in 1); Me is methyl).

Relative to the compound represented by the formula (II), magnesium can be used at 0.5 to 2 mol equivalents, and the compound represented by the formula: $R^2$—C(=O)—X wherein $R^2$ is as defined in 1); X is as defined as above or the formula: $R^2$—C(=O)—N(Me)(OMe) wherein $R^2$ is as defined in 1); Me is methyl can be used at 0.5 to 3 mol equivalents.

As the solvent, tetrahydrofuran or the like can be used.

A reaction temperature can be 0° C. to a reflux temperature of a solvent, and a reaction time can be 0.5 to 12 hours.

The second step is a step of asymmetric-reducing the compound represented by the formula (III) with an asymmetric reductive reagent in a solvent to produce the compound represented by the formula (IV). By subjecting the compound represented by the formula (IV) to the third step to the sixth step of the production method A, the compound represented by the formula (I) can be obtained.

Relative to the compound represented by the formula (III), the asymmetric reducing reagent can be used at 0.5 to 2 mol equivalents.

As the solvent, toluene, tetrahydrofuran and the like can be used alone, or by mixing them.

As the asymmetric reductive reagent, R-CBS or the like can be used.

R-CBS is an optically active compound represented by the formula:

[Chemical formula 10]

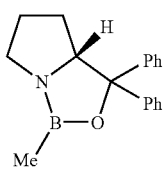

wherein Me is methyl; Ph is phenyl.

A reaction temperature can be −20° C. to a reflux temperature of a solvent, and a reaction time can be 0.5 to 12 hours.

The compound obtained in each step can be isolated and purified by a general method such as silica gel column chromatography, recrystallization, and/or distillation. Alternatively, the resulting compound can be also used in a next reaction without purification.

Production Method E

[Chemical formula 11]

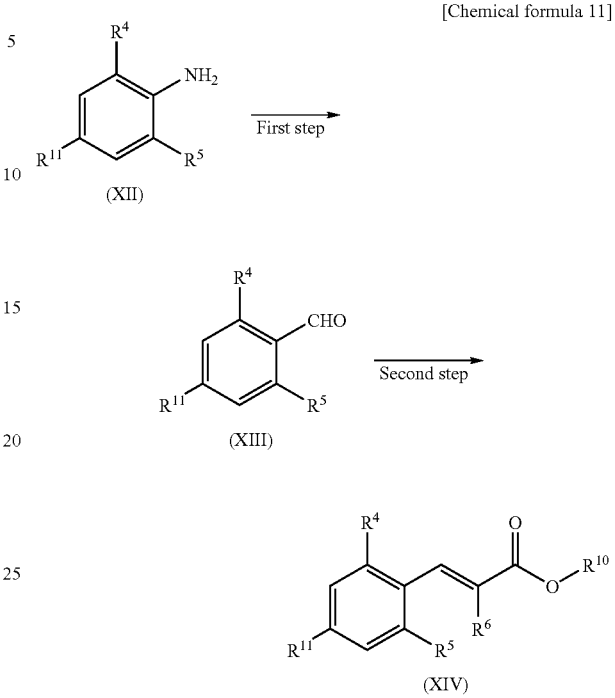

wherein $R^4$ and $R^5$ are as defined in 1); $R^{10}$ is as defined in a production method A; $R^{11}$ is a bromine atom or a iodine atom.

As a compound represented by the formula (XII) as a starting compound, a commercially available product can be used.

A production method E is a method of producing a compound represented by the formula (XIV) from the compound represented by the formula (XII) via a first step and a second step.

The first step is a step of producing a compound represented by the formula (XIII) by diazotizing the compound represented by the formula (XII) with sodium nitrite in a solvent in the presence of an acid, reacting this with alkyl acrylate, and ozonolysis the resulting compound.

Relative to the compound represented by the formula (XII), sodium nitride can be used at 0.5 to 3 mol equivalents, and alkyl acrylate can be used at 0.5 to 3 mol equivalents.

As the solvent in diazotization, acetone or the like can be used. As the solvent in ozonolysis, dichloromethane or the like can be used.

In diazotization and ozonolysis, each independently, a reaction temperature can be −78° C. to a reflux temperature of a solvent, and a reaction time can be 0.5 to 12 hours.

In the second step, using the same method as a production method B, the compound represented by the formula (XIV) can be obtained from the compound represented by the formula (XIII).

The compound obtained in each step can be isolated and purified by a general method such as silica gel column chromatography, recrystallization, and/or distillation. Alternatively, the resulting compound can be also used in a next reaction without purification.

Production Method F

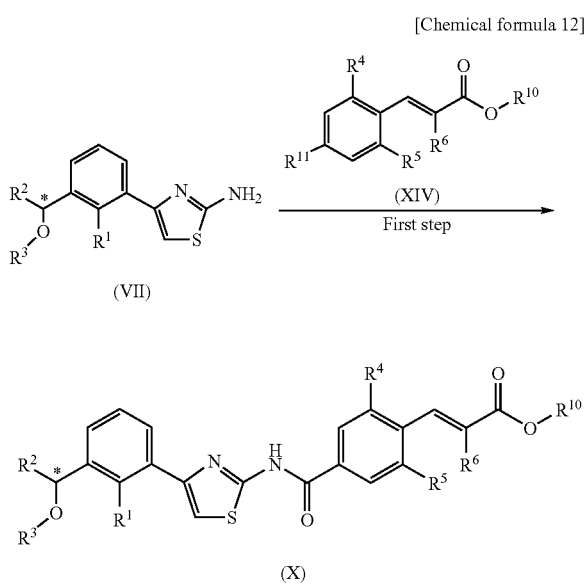

wherein $R^1$, $R^2$, $R^3$, $R^4$, $R^5$, and $R^6$ are as defined in 1); $R^{10}$ is as defined in a production method A; $R^{11}$ is a bromine atom or an iodine atom.

As the compound represented by the formula (VII) as a starting compound, the compound produced by a production method A can be used.

A production method F is a method of condensing the compound represented by the formula (VII) and the compound represented by the formula (XIV) to produce the compound represented by the formula (X). By subjecting the compound represented by the formula (X) to the sixth step of a production method A, the compound represented by the formula (I) can be obtained.

The present step can be conducted by using the same method as the method described in the second step of C method of International Publication WO 2005/014561.

The compound obtained in each step can be isolated and purified by a general method such as silica gel column chromatography, recrystallization, and/or distillation. Alternatively, the resulting compound can be also used in a next reaction without purification. Alternatively, an optically active compound is obtained by column chromatography using a chiral column, and each step may be performed using it.

Regarding the crystal of the optically active compound represented by the formula (I) produced by the aforementioned production methods, the crystal of the optically active compound represented by the formula (VII), and the crystal of the compound represented by the formula (IX), a X-ray diffraction pattern can be obtained by powder X-ray diffraction.

Since the crystal is stable, is easily handled for performing the above production steps, or producing a pharmaceutical composition containing, as an active ingredient, the optically active compound represented by the formula (I), and has a high purity, it is a useful crystal for producing a pharmaceutical composition.

Regarding the crystal of the optically active compound represented by the formula (I), the crystal of the optically active compound represented by the formula (VII), and the crystal of the compound represented by the formula (IX), a X-ray diffraction pattern is shown in Examples 3 to 5 described later (X-ray diffraction measurement condition: vacuum tube CuK α-ray, tubular voltage 40 Kv, tubular current 40 mA or 50 mA, d sin θ=nλ(n is an integer, d is spacing (unit: Angstrom), θ is diffraction angle (unit: degree))).

These crystals are characterized by values of each diffraction angle or spacing.

Herein, examples of the "pharmaceutically acceptable salt" include salts with alkali metals (such as lithium, sodium, and potassium), alkaline earth metals (such as magnesium and calcium), ammonium, organic bases and amino acid, or salts with inorganic acids (such as hydrochloric acid, hydrobromic acid, phosphoric acid, and sulfuric acid), and organic salts (such as acetic acid, citric acid, maleic acid, fumaric acid, benzenesulfonic acid, and p-toluenesulfonic acid). These salts can be formed by normally performed methods.

Herein, the "solvate" includes, for example, a solvate with an organic solvent, a hydrate and the like. When a solvate is formed, the compound may be coordinated with an arbitrarily number of solvent molecules.

The present pharmaceutical composition exhibits excellent thrombopoietin receptor agonist activity as described in Test Examples descried later, and can be used as an agent (platelet production regulating agent) for morbidity of a blood disease accompanied with an abnormality of the platelet number such as thrombocytopenia (thrombocytopenia after hematopoietic stem cell transplantation (such as bone marrow transplantation) and the like, thrombocytopenia after chemical therapy, hypoplastic anemia, myelodysplastic syndrome, acquired thrombocytopenia such as idiopathic thrombocytopenic purpura and the like, congenital thrombocytopenia such as thrombopoietin deficiency and the like, virus pneumonia (such as hepatitis C and the like), other hepatic disease (hepatocirrhosis)) and the like. The composition can be used for treating and/or preventing an abnormality of the platelet number due to administration of an anti-cancer agent for hematopoietic organ tumor, solid tumor or the like. The composition can be used for treating and/or preventing thrombocytopenia at surgical operation such as cardiovascular system (such as heart blood vessel) or the like.

When the present pharmaceutical composition is administered to a human for the purpose of treating the above diseases, it can be orally administered as powders, granules, tablets, capsules, pills, solutions or the like, or can be parenterally administered as injectables, suppositories, transdermal absorbing agents, inhalation or the like. In addition, an effective amount of the present compound is mixed, if necessary, with pharmaceutical additives such as excipients, binders, wetting agents, disintegrating agents, lubricants or the like which are suitable for its dosage form, thereby, a pharmaceutical preparation can be obtained. In the case of injectables, the compound together with a suitable carrier is subjected to sterilization treatment into preparations.

A dose is different depending on the stage of a disease, an administration route, an age or a weight of a patient and, when orally administered to an adult, is usually 0.01 to 100 mg/kg/day, preferably 0.02 to 10 mg/kg/day, most preferably 0.05 to 5 mg/kg/day.

The present invention will be explained in more detail below by way of Examples and Test Examples, but the present invention is not limited thereto.

In Examples, the following abbreviations are used.
R-CBS: Optically active compound represented by the formula:

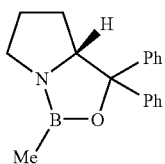

[Chemical formula 13]

wherein Me is methyl; Ph is phenyl.
Me: Methyl
DMF: N,N-dimethylformamide
THF: Tetrahydrofuran
DMSO: Dimethylformamide
HPLC: High pressure liquid chromatography

EXAMPLES

Reference Example 1

Synthesis of (RS)-(E)-3-(2,6-dichloro-4-{-4-[2-methyoxy-3-(1-methyloxyheptyl)phenyl]thiazol-2-ylcarbamoyl}phenyl)-2-methyl acrylic acid (B-1)

First Step: Synthesis of (RS)-2-bromo-6-(1-hydroxyheptyl)anisole (1)

To a THF solution of 2,6-dibromoanisole (10 g, 37.6 mmol) was added Mg (0.90 g, 37.6 mmol), and the mixture was heated and stirred at 40° C. Under ice-cooling, n-heptanal (47.2 g, 41.3 mmol) was added dropwise. Aqueous hydrochloric acid solution was added to the reaction mixture, this was extracted with ethyl acetate, and the solvent was distilled off to obtain 8.95 g of a compound (1).

NMR (CDCl$_3$) δ ppm: 7.45-7.48 (m, 1H), 7.35-7.38 (m, 1H), 7.01 (t, 1H, 8.1 Hz), 4.96-5.00 (m, 1H), 3.88 (s, 3H), 1.70-1.80 (m, 2H), 1.25-1.63 (m, 8H), 0.85-0.90 (m, 3H)

Second Step: Synthesis of (RS)-1-bromo-2-methyloxy-3-(1-methyloxyheptyl)benzene (2)

(RS)-2-bromo-6-(1-hydroxyheptyl)anisole (1, 5.36 g, 17.8 mmol) obtained in the first step and iodomethane (3.0 g, 21.3 mmol) were dissolved in THF, and sodium hydride (0.78 g, 19.6 mmol) was added thereto under ice-cooling. Under ice-cooling, hydrochloric acid was added, followed by extraction with ethyl acetate. After the solvent was distilled off, the residue was purified by silica gel chromatography to obtain 4.92 g of a compound (2).

[Chemical formula 14]

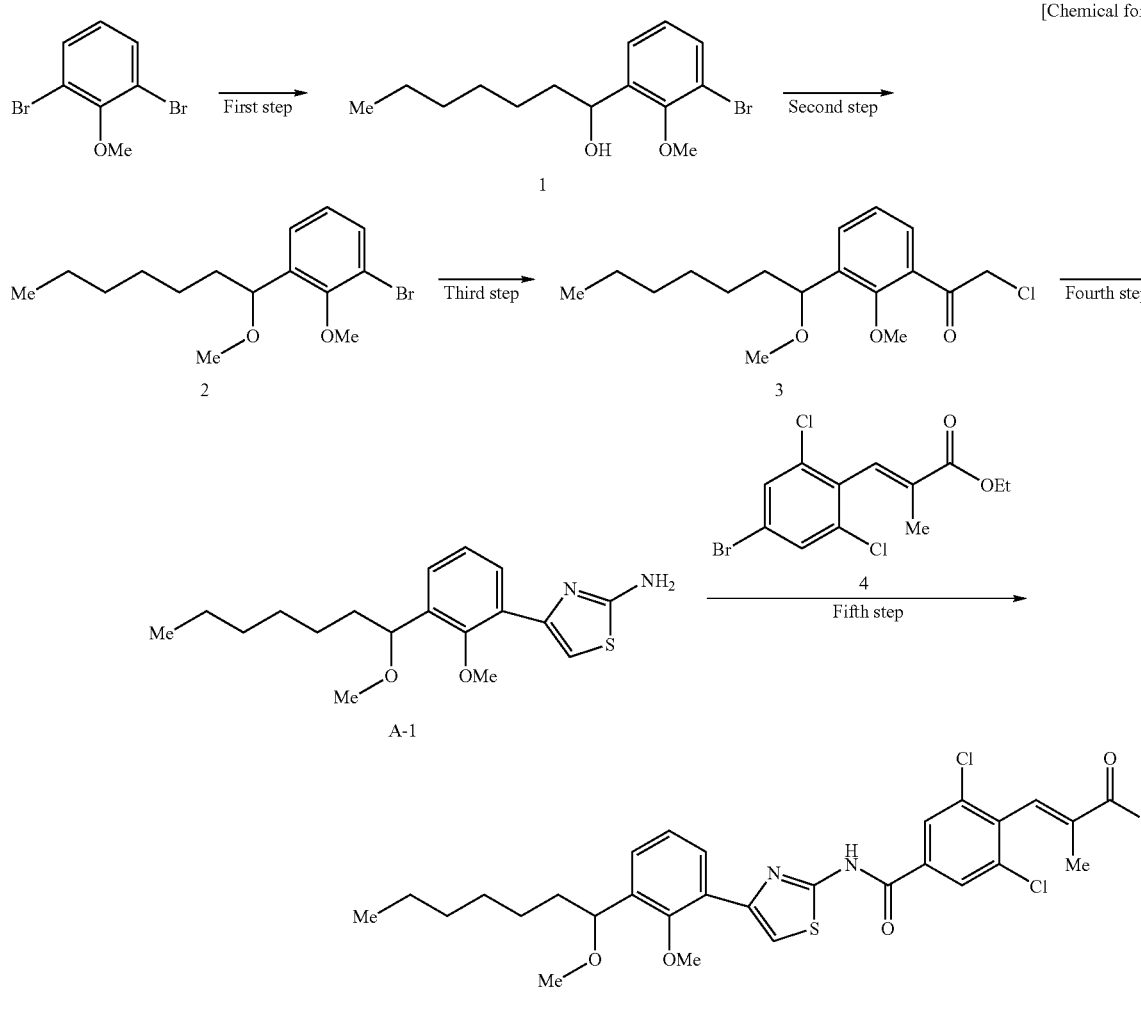

NMR (CDCl₃) δ ppm: 7.46 (d, 1H, J=8.1 Hz), 7.33 (d, 1H, J=4.5 Hz), 7.02 (t, 1H, J=7.5 Hz), 4.52 (dd, 1H, J=7.5 Hz, J=4.8 Hz), 3.85 (s, 3H), 3.21 (s, 3H), 1.27-1.80 (m, 10H), 0.84-0.90 (m, 3H)

Third Step: Synthesis of (RS)-2-chloro-1-[2-methyloxy-3-(1-methyloxypeptyl)phenyl]ethanone (3)

To a THF solution of (RS)-1-bromo-2-methyloxy-3-(1-methyloxyheptyl)benzene (2, 6.3 g, 20 mmol) obtained in the second step was added dropwise 2M isopropylmagnesium chloride (20 mL). 2-Chloro-N-methyloxy-N-methylacetamide (5.5 g) was added thereto, and the mixture was stirred at room temperature. To the reaction solution was added aqueous hydrochloride acid solution, followed by extraction with ethyl acetate. After the solvent was distilled off, the residue was purified by silica gel chromatography to obtain 2.80 g of a compound (3).

NMR (CDCl₃) δ ppm: 7.58-7.61 (m, 1H), 7.51-7.54 (m, 1H), 7.22-7.27 (m, 1H), 4.72 (dd, 2H, J=20.8 Hz, 15.9 Hz), 4.54 (dd, 1H, J=8.1 Hz, 4.8 Hz), 3.78 (s, 3H), 3.22 (s, 3H), 1.14-1.77 (m, 10H), 0.84-0.90 (m, 3H)

Fourth Step: Synthesis of (RS)-4-[2-methyloxy-3-(1-methyloxyheptyl)phenyl]thiazol-2-ylamine (A-1)

(RS)-2-chloro-1-[2-methyloxy-3-(1-methyloxypeptyl)phenyl]ethanone (3, 0.28 g, 0.89 mmol) obtained in the third step and thiourea (0.10 g, 0.89 mmol) were dissolved in ethanol, and the solution was heated and stirred. To the reaction solution was added an aqueous saturated sodium bicarbonate solution, followed by extraction with ethyl acetate. After the solvent was distilled off, the residue was purified by silica gel chromatography to obtain 0.23 g of a compound (A-1).

NMR (CDCl₃) δ ppm: 7.75 (dd, 1H, J=1.8 Hz, 7.5 Hz), 7.34 (dd, J=1.8 Hz, 7.5 Hz, 1H), 7.19 (t, 1H, J=7.5 Hz), 7.08 (s, 1H), 5.41 (brs, 2H), 4.57-4.61 (m, 1H), 3.65 (s, 3H), 3.23 (s, 3H), 1.24-1.77 (m, 10H), 0.84-0.89 (m, 3H)

Fifth Step: Synthesis of (RS)-(E)-3-(2,6-dichloro-4-{4-[2-methyloxyl-3-(1-methyloxyheptyl)phenyl]thiazol-2-ylcarbamoyl}phenyl)-2-methylacrylic acid (B-1)

To a DMF (6 mL) solution of (RS)-4-[2-methyloxy-3-(1-methyloxyheptyl)phenyl]thiazol-2-ylamine (A-1, 330 mg) obtained in the fourth step, ethyl 3-(4-bromo-2,6-dichlorophenyl)-2-methylacrylate (4, 338 mg) synthesized in Reference Example 18 described later, and dichlorobistriphenylphosphinepalladium (42 mg) was added triethylamine (0.56 mL), and the mixture was stirred at 85° C. for 16 hours under the carbon monooxide atmosphere. The reaction solution was added to water, followed by extraction with ethyl acetate. The organic layer was washed with water, washed with an aqueous saturated sodium chloride solution, and dried with magnesium sulfate. After the solvent was distilled off, purification by column chromatography (hexane:ethyl acetate=4:1) afforded 540 mg of a solid. This solid was dissolved in THF (3 mL), methanol (3 mL), and a 2 mol/L sodium hydroxide aqueous solution (3 mL) were added, and the mixture was stirred at room temperature. The reaction solution was made acidic with hydrochloric acid, followed by extraction with ethyl acetate. The organic layer was washed with water, washed with an aqueous saturated sodium chloride solution, and dried over magnesium sulfate. After the solvent was distilled off, recrystallization with ethyl acetate afforded 370 mg of a compound (B-1).

NMR (DMSO-d6) δ ppm: 12.99 (brs, 1H), 8.29 (s, 2H), 7.91 (dd, 1H, J=2.1 Hz, 7.2 Hz), 7.72 (s, 1H), 7.41 (d, 1H, J=1.5 Hz), 7.24-7.33 (m, 2H), 4.55-4.60 (m, 1H), 3.62 (s, 3H), 3.16 (s, 3H), 1.69 (s, 3H), 1.25-1.69 (m, 10H), 0.83-0.87 (m, 3H)

Using the same method as the synthesis method described in Reference Example 1, compounds (A-2) to (A-16), and compounds (B-2) to (B-16) were synthesized.

Reference Example 2

Synthesis of (RS)-(E)-3-(2,6-dichloro-4-{4-[2-methyloxy-3-(1-pentyloxyethyl)phenyl]thiazol-2-ylcarbamoyl}phenyl)-2-methylacrylic acid (B-2)

(RS)-4-[2-methyloxy-3-(1-pentyloxyethyl)phenyl]thiazol-2-ylamine (A-2)

NMR (CDCl₃) δ ppm: 7.74 (dd, 1H, J=2.1 Hz, 7.8 Hz), 7.41 (dd, 1H, J=2.1 Hz, 7.8 Hz), 7.19 (t, 1H, J=7.8 Hz), 7.07 (s, 1H), 5.49 (brs, 2H), 4.85 (q, 1H, J=6.3 Hz), 3.65 (s, 3H), 3.28-3.33 (m, 2H), 1.54-1.58 (m, 1H), 1.45 (d. 3H, J=6.6 Hz), 1.24-1.30 (m, 4H), 0.85-0.90 (m, 3H)

Compound (B-2)

NMR (DMSO-d6) δ ppm: 8.32 (s, 2H), 7.65 (s, 1H), 7.48-7.60 (m, 2H), 7.43 (s, 1H), 7.23-7.27 (m, 1H), 4.87 (q, 1H, J=6.3 Hz), 3.55 (s, 3H), 1.87 (s, 1.55-1.62 (m, 2H), 1.48 (d, 3H, J=6.3 Hz), 1.26-1.38 (m, 4H), 0.86-0.90 (m, 3H)

Reference Example 3

Synthesis of (RS)-(E)-3-(2,6-dichloro-4-{4-[3-(1-hexyloxyethyl)-2-methyloxyphenyl]thiazol-2-ylcarbamoyl}phenyl)-2-methylacrylic acid (B-3)

(RS)-4-[3-(1-hexyloxyethyl)-2-methyloxyphenyl]thiazol-2-ylamine (A-3)

NMR (CDCl₃) δ ppm: 7.75 (dd, 1H, J=1.2 Hz, 7.8 Hz), 7.41 (dd, 1H, J=1.2 Hz, 7.8 Hz), 7.20 (t, 1H, J=7.8 Hz), 7.08 (s, 1H), 5.48 (brs, 2H), 4.85 (q, 1H, J=6.0 Hz), 3.66 (s, 3H), 3.28-3.33 (m, 2H), 1.52-1.59 (m, 1H), 1.45 (d, 3H, J=6.3 Hz), 1.24-1.34 (m, 6H), 0.85-0.89 (m, 3H)

Compound (B-3)

NMR (DMSO-d6) δ ppm: 12.97 (brs, 1H), 8.29 (s, 2H), 7.90 (dd, 1H, J=1.8 Hz, 7.5 Hz), 7.72 (s, 1H), 7.35-7.40 (m, 2H), 7.26 (t, 1H, J=7.5 Hz), 4.82 (q, 1H, J=6.3 Hz), 3.62 (s, 3H), 3.16-3.37 (m, 2H), 1.69 (s, 3H), 1.18-1.51 (m, 11H), 0.82-0.87 (m, 3H)

Reference Example 4

Synthesis of (RS)-(E)-3-(2,6-dichloro-4-{-4-[2-methyloxy-3-(1-methyloxyhexyl)phenyl]thiazol-2-ylcarbamoyl}phenyl)-2-methylacrylic acid (B-4)

NMR (CDCl₃) δ ppm: 7.75 (dd, 1H, J=1.8 Hz, 7.8 Hz), 7.34 (dd, 1H, J=1.8 Hz, 7.8 Hz), 7.19 (t, 1H, J=7.8 Hz), 7.08 (s, 1H), 5.48 (brs, 2H), 4.57-4.61 (m, 1H), 3.65 (s, 3H), 3.23 (s, 3H), 1.26-1.77 (m, 8H), 0.85-0.90 (m, 3H)

Compound (B-4)

NMR (DMSO-d6) δ ppm: 12.98 (brs, 1H), 8.29 (s, 2H), 7.91 (dd, 1H, J=2.4 Hz, 7.5 Hz), 7.72 (s, 1H), 7.40 (s, 1H), 7.24-7.33 (m, 2H), 4.56-4.60 (m, 1H), 3.62 (s, 3H), 3.16 (s, 3H), 1.69 (s, 3H), 1.25-1.69 (m, 8H), 0.83-0.88 (m, 3H)

Reference Example 5

Synthesis of (RS)-(E)-(2,6-dichloro-4-{-4-[3-(1-ethyloxyhexyl)-2-methyloxyphenyl]thiazol-2-ylcarbamoyl}phenyl)-2-methylacrylic acid (B-5)

(RS)-4-[3-(1-methyloxyhexyl)-2-methyloxyphenyl] thiazol-2-ylamine (A-5)

NMR (CDCl$_3$) δ ppm: 7.73 (dd, 1H, J=1.8 Hz, 7.5 Hz), 7.38 (dd, 1H, J=1.8 Hz, 7.5 Hz), 7.18 (t, 1H, J=7.5 Hz), 7.07 (s, 1H), 5.48 (brs, 2H), 4.66-4.70 (m, 1H), 3.64 (s, 3H), 3.31-3.42 (m, 2H), 1.16-1.78 (m, 11H), 0.85-0.90 (m, 3H)
Compound (B-5)
NMR (DMSO-d6) δ ppm: 12.97 (brs, 1H), 8.29 (s, 2H), 7.89 (dd, 1H, J=1.8 Hz, 7.8 Hz), 7.71 (s, 1H), 7.22-7.40 (m, 4H), 4.65-4.69 (m, 1H), 3.58 (s, 3H), 3.17 (d, 2H, J=4.5 Hz), 1.69 (s, 3H), 1.03-1.69 (m, 11H), 0.84-0.88 (m, 3H)

Reference Example 6

Synthesis of (RS)-(E)-3-(2,6-dichloro-4-{4-[3-(1-ethyloxypentyl)-2-methyloxyphenyl]thiazol-2-ylcarbamoyl}phenyl)-2-methylacrylic acid (B-6)

(RS)-4-[3-(1-ethyloxypentyl)-2-methyloxyphenyl] thiazol-2-ylamine (A-6)

NMR (CDCl$_3$) δ ppm: 7.75 (dd, 1H, J=7.5 Hz, 1.8 Hz), 7.34 (dd, 1H, J=7.5 Hz, 1.8 Hz), 7.15 (t, 1H, J=7.5 Hz), 7.08 (s, 1H), 5.26 (brs, 2H), 4.67-4.70 (m, 1H), 3.64 (s, 3H), 3.27 (q, 2H, J=7.0 Hz), 1.56-1.68 (m, 2H), 1.20-1.50 (m, 4H), 1.10 (t, 3H, J=7.0 Hz), 0.85 (t, 3H, J=7.0 Hz)
Compound (B-6)
NMR (DMSO-d6) δ ppm: 12.98 (brs, 1H), 8.28 (s, 2H), 7.92 (d, 1H, J=7.5 Hz), 7.71 (s, 1H), 7.41 (s, 1H), 7.33 (d, 1H, J=7.6 Hz), 7.25 (t, 1H, J=7.6 Hz), 4.67 (t, 1H, J=6.5 Hz), 3.60 (s, 3H), 3.26 (q, 2H, J=7.0 Hz), 1.68 (s, 3H), 1.56-1.68 (m, 2H), 1.20-1.50 (m, 4H), 1.10 (t, 3H, J=7.0 Hz), 0.85 (t, 3H, J=7.0 Hz).

Reference Example 7

Synthesis of (RS)-(E)-3-(2,6-dichloro-4-{4-[2-methyloxy-3-(1-propyloxypentyl)phenyl]thiazol-2-ylcarbamoyl}phenyl)-2-methylacrylic acid (B-7)

(RS)-4-[2-methyloxy-3-(1-propyloxypentyl)phenyl] thiazol-2-ylamine (A-7)

NMR (CDCl$_3$) δ ppm: 7.75 (dd, 1H, J=7.5 Hz, 1.8 Hz), 7.34 (dd, 1H, J=7.5 Hz, 1.8 Hz), 7.15 (t, 1H, J=7.5 Hz), 7.08 (s, 1H), 5.26 (brs, 2H), 4.67-4.70 (m, 1H), 3.64 (s, 3H), 3.27 (q, 2H, J=7.0 Hz), 1.56-1.68 (m, 2H), 1.50-1.60 (m, 2H), 1.20-1.50 (m, 4H), 0.87 (t, 3H, J=7.0 Hz), 0.85 (t, 3H, J=7.0 Hz).
Compound (B-7)
NMR (DMSO-d6) δ ppm: 12.98 (brs, 1H), 8.28 (s, 2H), 7.90 (d, 1H, J=7.5 Hz), 7.71 (s, 1H), 7.41 (s, 1H), 7.33 (d, 1H, J=7.6 Hz), 7.25 (t, 1H, J=7.6 Hz), 4.67 (t, 1H, J=6.5 Hz), 3.61 (s, 3H), 3.20 (t, 2H, J=7.0 Hz), 1.68 (s, 3H), 1.56-1.68 (m, 2H), 1.50-1.60 (m, 2H), 1.20-1.50 (m, 4H), 0.90 (t, 3H, J=7.0 Hz), 0.85 (t, 3H, J=7.0 Hz).

Reference Example 8

Synthesis of (RS)-(E)-3-(2,6-dichloro-4-{-4-[3-(2,2-dimethylpropyl-1-ethyloxy)-2-methyloxyphenyl] thiazol-2-ylcarbamoyl}phenyl)-2-methylacrylic acid (B-8)

(RS)-4-[3-(2,2-dimethylpropyl-1-ethyloxy)-2-methyloxyphenyl]thiazol-2-ylamine (A-8)

NMR (CDCl$_3$) δ ppm: 7.73 (dd, 1H, J=7.5 Hz, 1.8 Hz), 7.34 (dd, 1H, J=7.5 Hz, 1.8 Hz), 7.13 (t, 1H, J=7.5 Hz), 7.08 (s, 1H), 5.26 (brs, 2H), 4.37 (s, 1H), 3.60 (s, 3H), 3.22-3.38 (m, 2H), 1.08 (t, 3H, J=7.0 Hz), 0.90 (s, 9H).
Compound (B-8)
NMR (DMSO-d6) δ ppm: 12.98 (brs, 1H), 8.28 (s, 2H), 7.90 (d, 1H, J=7.5 Hz), 7.68 (s, 1H), 7.40 (s, 1H), 7.29 (d, 1H, J=7.6 Hz), 7.25 (t, 1H, J=7.6 Hz), 4.40 (s, 1H), 3.61 (s, 3H), 3.30 (q, 2H, J=7.0 Hz), 1.68 (s, 3H), 1.15 (t, 3H, J=7.0 Hz), 0.89 (s, 9H).

Reference Example 9

Synthesis of (RS)-(E)-3-(2,6-dichloro-4-{-4-[3-(2,2-dimethyl-1-propyloxypropyl)-2-methyloxyphenyl] thiazol-2-ylcarbamoyl}phenyl)-2-methylacrylic acid (B-9)

(RS)-4-[3-(2,2-dimethyl-1-propyloxypropyl)-2-methyloxyphenyl]thiazol-2-ylamine (A-9)

NMR (CDCl$_3$) δ ppm: 7.74 (dd, 1H, J=7.5 Hz, 1.8 Hz), 7.32 (dd, 1H, J=7.5 Hz, 1.8 Hz), 7.13 (t, 1H, J=7.5 Hz), 7.08 (s, 1H), 5.26 (brs, 2H), 4.37 (s, 1H), 3.60 (s, 3H), 3.22-3.38 (m, 2H), 1.56-1.66 (m, 2H), 0.93 (t, 3H, J=7.0 Hz), 0.90 (s, 9H).
Compound (B-9)
NMR (DMSO-d6) δ ppm: 12.98 (brs, 1H), 8.28 (s, 2H), 7.92 (d, 1H, J=7.5 Hz), 7.68 (s, 1H), 7.40 (s, 1H), 7.31 (d, 1H, J=7.6 Hz), 7.27 (t, 1H, J=7.6 Hz), 4.40 (s, 1H), 3.61 (s, 3H), 3.20 (t, 2H, J=7.0 Hz), 1.68 (s, 3H), 1.55-165 (m, 2H), 0.90 (t, 3H, J=7.0 Hz), 0.87 (s, 9H).

Reference Example 10

Synthesis of (RS)-(E)-3-(2,6-dichloro-4-{4-[2-methyloxy-3-(1-propyloxybutyl)phenyl]thiazol-2-ylcarbamoyl}phenyl)-2-methylacrylic acid (B-10)

(RS)-4-[2-methyloxy-3-(1-propyloxybutyl)phenyl] thiazol-2-ylamine (A-10)

NMR (CDCl$_3$) δ ppm: 7.74 (d, J=7.5 Hz, 1H), 7.36 (d, 1H, J=7.8 Hz), 7.20 (t, 1H, J=7.5 Hz), 7.08 (s, 1H), 5.15 (brs, 2H), 4.67-4.74 (m, 1H), 3.64 (s, 3H), 3.19-3.36 (m, 2H), 1.50-1.80 (m, 6H), 0.86-0.98 (m, 6H)
Compound (B-10)
NMR (DMSO-d6) δ ppm: 13.00 (brs, 2H), 8.29 (s, 2H), 7.90 (d, 1H, J=7.5 Hz), 7.72 (s, 1H), 7.24-7.43 (m, 3H), 4.65-4.72 (m, 1H), 3.61 (s, 3H), 3.23 (t, 2H, J=6.3 Hz), 1.30-1.80 (m, 9H), 0.84-0.98 (m, 6H)

Reference Example 11

Synthesis of (RS)-(E)-3-(4-{4-[3-(1-butyloxybutyl)-2-methyloxyphenyl]thiazol-2-ylcarbamoyl}-2,6-dichlorophenyl)-2-methylacrylic acid (B-11)

(RS)-4-[3-(1-butyloxybutyl-2-methyloxyphenyl]thiazol-2-ylamine (A-11)

NMR (CDCl$_3$) δ ppm: 7.74 (d, J=7.5 Hz, 1H), 7.36 (d, 1H, J=7.8 Hz), 7.20 (t, 1H, J=7.5 Hz), 7.08 (s, 1H), 5.15 (brs, 2H), 4.67-4.74 (m, 1H), 3.64 (s, 3H), 3.19-3.36 (m, 2H), 1.50-1.80 (m, 8H), 0.86-0.98 (m, 6H)

Compound (B-11)

NMR (DMSO-d6) δ ppm: 13.01 (brs, 2H), 8.29 (s, 2H), 7.90 (d, 1H, J=7.5 Hz), 7.72 (s, 1H), 7.23-7.44 (m, 3H), 4.65-4.72 (m, 1H), 3.61 (s, 3H), 3.27 (t, 2H, J=6.3 Hz), 1.30-1.78 (m, 11H), 0.83-0.98 (m, 6H)

Reference Example 12

Synthesis of (RS)-(E)-3-(2,6-dichloro-4-{4-[3-(1-ethyloxy-3-methylbutyl)-2-methyloxyphenyl]thiazol-2-ylcarbamoyl}phenyl)-2-methylacrylic acid (B-12)

(RS)-4-[3-(1-ethyloxy-3-methyloxybutyl)-2-methyloxyphenyl]thiazol-2-ylamine (A-12)

NMR (CDCl$_3$) δ ppm: 7.74 (d, 1H, J=7.5 Hz), 7.36 (d, 1H, J=7.8 Hz), 7.20 (t, 1H, J=7.5 Hz), 7.08 (s, 1H), 5.15 (brs, 2H), 4.76-4.84 (m, 1H), 3.64 (s, 3H), 3.30-3.42 (m, 2H), 1.50-1.80 (m, 6H), 0.92-1.02 (m, 6H)

Compound (B-13)

NMR (DMSO-d6) δ ppm: 13.00 (brs, 2H), 8.29 (s, 2H), 7.90 (d, 1H, J=7.5 Hz), 7.72 (s, 1H), 7.23-7.44 (m, 3H), 4.65-4.72 (m, 1H), 3.62 (s, 3H), 3.27 (t, 2H, J=6.3 Hz), 1.78-1.90 (m, 1H), 1.60-74 (m, 4H), 1.30-1.40 (m, 1H), 1.11 (t, 3H, J=6.9 Hz), 0.97 (d, 3H, J=6.3 Hz), 0.93 (d, 3H, J=6.3 Hz)

Reference Example 13

Synthesis of (RS)-(E)-3-(2,6-dichloro-4-{4-[2-methyloxy-3-(2-methyl-1-propyloxypropyl)phenyl]thiazol-2-ylcarbamoyl}phenyl)-2-methylacrylic acid (B-13)

(RS)-4-[2-methyloxy-3-(2-methyl-1-propyloxypropyl)phenyl]thiazol-2-ylamine (A-13)

NMR (CDCl$_3$) δ ppm: 7.74 (d, 1H, J=7.5 Hz), 7.36 (d, 1H, J=7.8 Hz), 7.20 (t, 1H, J=7.5 Hz), 7.08 (s, 1H), 5.20 (brs, 2H), 4.36 (d, 1H, J=6.9 Hz), 3.60 (s, 3H), 3.15-3.34 (m, 2H), 1.90-2.02 (m, 1H), 1.50-1.63 (m, 2H), 1.02 (d, 3H, J=6.6 Hz), 0.91 (t, 3H, J=7.5 Hz), 0.83 (d, 3H, J=6.6 Hz)

Compound (B-13)

NMR (DMSO-d6) δ ppm: 13.00 (brs, 2H), 8.29 (s, 2H), 7.88 (d, 1H, J=7.5 Hz), 7.70 (s, 1H), 7.20-7.42 (m, 3H), 4.38 (dz, 1H, J=5.1 Hz), 3.60 (s, 3H), 3.20-3.27 (m, 2H), 1.85-1.95 (m, 1H), 1.69 (s, 3H), 1.44-0.55 (m, 2H), 0.96 (d, 3H, J=4.8 Hz), 0.88 (t, 3H, J=5.7 Hz), 0.81 (d, 3H, J=5.1 Hz)

Reference Example 14

Synthesis of (RS)-(E)-3-(4-{4-[3-(1-butyloxypropyl)-2-methyloxyphenyl]thiazol-2-ylcarbamoyl}-2,6-dichlorophenyl)-2-methylacrylic acid (B-14)

(RS)-4-[3-(1-butyloxypropyl)-2-methyloxyphenyl]thiazol-2-ylamine (A-14)

NMR (CDCl$_3$) δ ppm: 7.73 (dd, 1H, J=1.8 Hz, 7.8 Hz), 7.36 (dd, 1H, J=1.8 Hz, 7.8 Hz), 7.17 (t, 1H, J=7.8 Hz), 7.07 (s, 1H), 5.39 (brs, 2H), 4.58-4.62 (m, 1H), 3.64 (s, 3H), 3.24-3.37 (m, 2H), 1.30-1.86 (m, 6H), 0.98 (t, 3H, J=7.5 Hz), 0.89 (t, 3H, J=7.5 Hz)

Compound (B-14)

NMR (DMSO-d6) δ ppm: 13.00 (brs, 1H), 8.29 (s, 2H), 7.89-7.92 (m, 1H), 7.72 (s, 1H), 7.40 (s, 1H), 7.23-7.34 (m, 2H), 4.57-4.61 (m, 1H), 3.61 (s, 3H), 3.26-3.30 (m, 3H), 1.69 (s, 3H), 1.26-1.78 (m, 6H), 0.92 (t, 3H, J=7.2 Hz), 0.86 (t, 3H, J=7.2 Hz)

Reference Example 15

Synthesis of (RS)-(E)-3-(2,6-dichloro-4-{4-[2-methyloxy-3-(1-pentyloxypropyl)phenyl]thiazol-2-ylcarbamoyl}phenyl)-2-methylacrylic acid (B-15)

(RS)-4-[2-methyloxy-3-(1-pentyloxypropyl)phenyl]thiazol-2-ylamine (A-15)

NMR (CDCl$_3$) δ ppm: 7.73 (dd, 1H, J=1.8 Hz, 7.8 Hz), 7.36 (dd, 1H, J=1.8 Hz, 7.8 Hz), 7.17 (t, 1H, J=7.8 Hz), 7.07 (s, 1H), 5.33 (brs, 2H), 4.58-4.62 (m, 1H), 3.64 (s, 3H), 3.23-3.37 (m, 2H), 1.22-1.86 (m, 8H), 0.98 (t, 3H, J=7.2), 0.85-0.90 (m, 3H)

Compound (B-15)

NMR (DMSO-d6) δ ppm: 13.00 (brs, 1H), 8.29 (s, 2H), 7.89-7.92 (m, 1H), 7.72 (s, 1H), 7.40 (s, 1H), 7.23-7.34 (m, 2H), 4.56-4.61 (m, 1H), 3.61 (s, 3H), 3.25-3.39 (m, 3H), 1.69 (s, 3H), 1.18-1.77 (m, 8H), 0.92 (t, 3H, J=7.2 Hz), 0.85 (t, 3H, J=7.2 Hz)

Reference Example 16

Synthesis of (RS)-(E)-3-(2,6-dichloro-4-{4-[2-methyloxy-3-(1-methyloxy-5-methylhexyl)phenyl]thiazol-2-ylcarbamoyl}phenyl)-2-methylacrylic acid (B-16)

Compound (B-16)

NMR (DMSO-d6) δ ppm: 12.98 (brs, 2H), 9.29 (s, 1H), 7.89-7.92 (m, 1H), 7.72 (s, 1H), 7.41 (s, 1H), 7.24-7.37 (m, 3H), 4.53-4.57 (m, 1H), 3.61 (s, 3H), 3.16 (s, 3H), 0.87-1.72 (m, 16H).

Reference Example 17

Synthesis of (E)-3-(4-bromo-2,6-dichlorophenyl)-2-methylacrylic acid ethyl (4)

[Chemical formula 15]

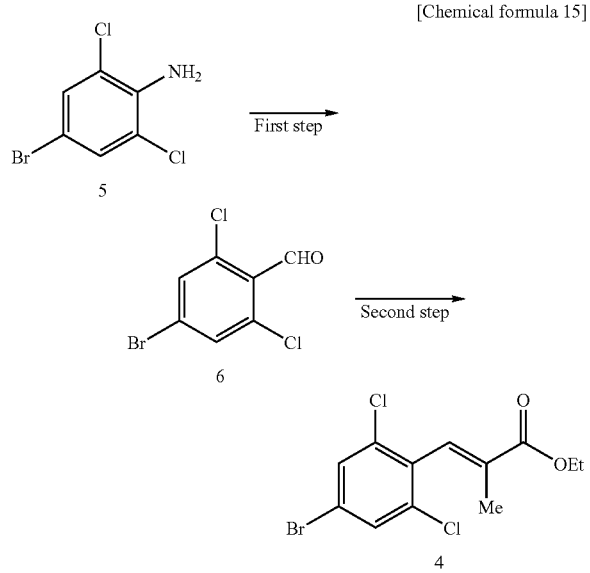

First Step: Synthesis of 4-bromo-2,6-dichlorobenzaldehyde (6)

4-Bromo-2,6-dichloroaniline (5, 80 g) was dissolved in acetone (640 mL), and a 48% hydrogen bromide aqueous solution (120 mL) was added, followed by stirring at 0° C. A sodium nitrite (32 g) aqueous solution (160 mL) was added dropwise thereto, the mixture was stirred for 30 minutes, and methyl acrylate (200 mL), and water (200 mL) were added, followed by stirring for 1 hour. At room temperature, cuprous oxide (2 g) was added, followed by stirring for 2 hours. The reaction solution was extracted with ethyl acetate, and purified by column chromatography to obtain methyl (E)-3-(4-bromo-2,6-dichlorophenyl)acrylate (48.5 g). Methyl (E)-3-(4-bromo-2,6-dichlorophenyl)acrylate (48.5 g) was dissolved in dichloromethane, an ozone gas was introduced at −70° C., and ozone oxidation was performed. To the reaction solution was added dimethyl sulfide (40 mL), and this was extracted with ethyl acetate to obtain 4-bromo-2,6-dichlorobenzaldehyde (6, 37.2 g).

NMR (CDCl$_3$) δ ppm: 10.42 (s, 1H), 7.58 (s, 2H)

Second Step: Synthesis of ethyl (E)-3-(4-bromo-2,6-dichlorophenyl)-2-methylacrylate (4)

Triethylphosphonopropionate (26.3 g) was dissolved in THF (150 mL), a THF solution of sodium hydride (6.3 g), and 4-bromo-2,6-dichlorobenzaldehyde (6, 20 g) obtained in the first step was added dropwise, and the mixture was stirred for 2 hours. The reaction solution was extracted with ethyl acetate, and purified by column chromatography to obtain ethyl (E)-3-(4-bromo-2,6-dichlorophenyl)-2-methylacrylate (6, 21.2 g).

Melting point: 32° C.
NMR (CDCl$_3$) δ ppm: 7.52 (s, 2H), 7.35 (s, 1H), 4.28 (q, 2H, J=7.0 Hz), 1.76 (s, 3H), 1.33 (t, 3H, J=7.0 Hz)

Example 1

Synthesis of (R)-(E)-3-(2,6-dichloro-4-{4-[2-methyloxy-3-(1-methyloxyheptyl)phenyl]thiazol-2-ylcarbamoyl}phenyl)-2-methylacrylic acid (C-1A) and (S)-(E)-3-(2,6-dichloro-4-{4-[2-methyloxy-3-(1-methyloxyheptyl)-phenyl]thiazol-2-ylcarbamoyl}phenyl)-2-methylacrylic acid (C-1B)

(RS)-(E)-3-(2,6-dichloro-4-{4-[2-methyloxy-3-(1-methyloxyhexyl)phenyl]thiazol-2-ylcarbamoyl}phenyl)-2-methylacrylic acid (B-1) obtained in Reference Example 1 was separated by HPLC column OJ-RH (registered trademark) manufactured by DAICEL (as an eluting solvent, a mixed solvent of acetonitrile, water, and trifluoroacetic acid) was to obtain an optically active compound (C-1A) and an optically active compound (C-1B).

Optically Active Compound (C-1A)
Melting point: 162-164° C.
NMR (DMSO-d6) δ ppm: 12.99 (brs, 1H), 8.29 (s, 2H), 7.91 (dd, 1H, J=2.1 Hz, 7.2 Hz), 7.72 (s, 1H), 7.41 (d, 1H, J=1.5 Hz), 7.24-7.33 (m, 2H), 4.55-4.60 (m, 1H), 3.62 (s, 3H), 3.16 (s, 3H), 1.69 (s, 3H), 1.25-1.69 (m, 10H), 0.83-0.87 (m, 3H)
Optical rotation: +25.6 degrees (DMSO, c=1.000, 25° C.)
Optically Active Compound (C-1B)
Melting point: 161-164° C.
NMR (DMSO-d6) δ ppm: 12.99 (brs, 1H), 8.29 (s, 2H), 7.91 (dd, 1H, J=2.1 Hz, 7.2 Hz), 7.72 (s, 1H), 7.41 (d, 1H, J=1.5 Hz), 7.24-7.33 (m, 2H), 4.55-4.60 (m, 1H), 3.62 (s, 3H), 3.16 (s, 3H), 1.69 (s, 3H), 1.25-1.69 (m, 10H), 0.83-0.87 (m, 3H)
Optical rotation: −25.6 degrees (DMSO, c=1.000, 25° C.)

Example 2

Synthesis of (R)-(E)-3-(2,6-dichloro-4-{4-[3-(1-hexyloxyethyl)-2-methyloxyphenyl]thiazol-2-ylcarbamoyl}phenyl)-2-methylacrylic acid (C-3A) and (S)-(−)-(E)-3-(2,6-dichloro-4-{4-[3-(1-hexyloxyethyl)-2-methyloxyphenyl]thiazol-2-ylcarbamoyl}phenyl)-2-methylacrylic acid (C-3B)

According to the same method as in Example 1, an optically active compound (C-3A) and an optically active compound (C-3B) were synthesized from (RS)-(E)-3-(2,6-dichloro-4-{4-[3-(1-hexyloxyethyl)-2-methyloxyphenyl]thiazol-2-ylcarbamoyl}phenyl)-2-methylacrylic acid (B-3) obtained in Reference Example 3.

Optically Active Compound (C-3A)
Melting point: 139-141° C.
NMR (DMSO-d6) δ ppm: 12.97 (brs, 1H), 8.29 (s, 2H), 7.90 (dd, 1H, J=1.8 Hz, 7.5 Hz), 7.72 (s, 1H), 7.35-7.40 (m, 2H), 7.26 (t, 1H, J=7.5 Hz), 4.82 (q, 1H, J=6.3 Hz), 3.62 (s, 3H), 3.16-3.37 (m, 2H), 1.69 (s, 3H), 1.18-1.51 (m, 11H), 0.82-0.87 (m, 3H)
Optical rotation +4.5 degrees (DMSO, c=1.001, 25° C.)
Optically Active Compound (C-3B)
Melting point: 142-145° C.
NMR (DMSO-d6) δ ppm: 12.97 (brs, 1H), 8.29 (s, 2H), 7.90 (dd, 1H, J=1.8 Hz, 7.5 Hz), 7.72 (s, 1H), 7.35-7.40 (m, 2H), 7.26 (t, 1H, J=7.5 Hz), 4.82 (q, 1H, J=6.3 Hz), 3.62 (s, 3H), 3.16-3.37 (m, 2H), 1.69 (s, 3H), 1.18-1.51 (m, 11H), 0.82-0.87 (m, 3H)
Optical rotation −4.5 degrees (DMSO, c=1.001, 25° C.)

Example 3
Synthesis of (C-1B)
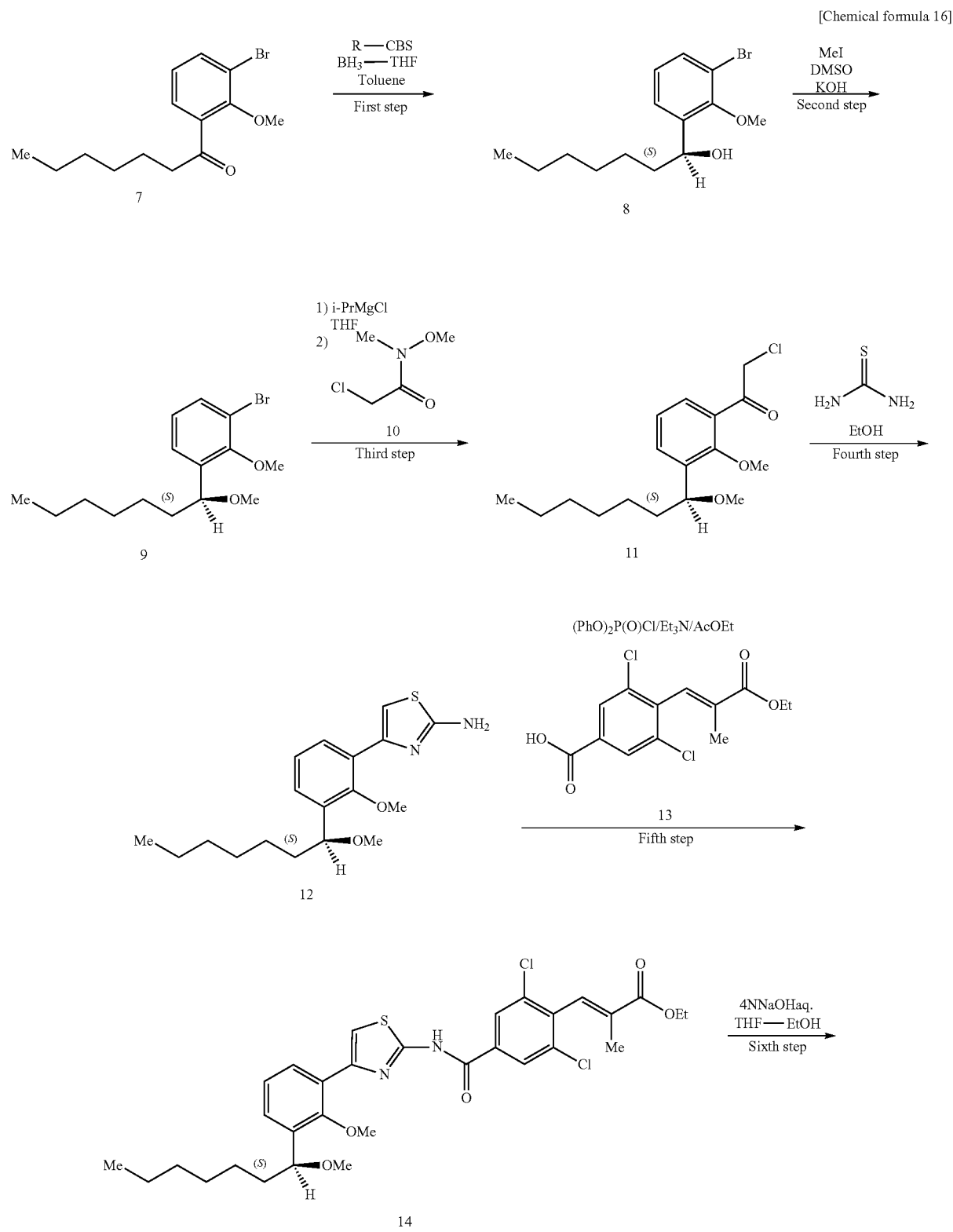
[Chemical formula 16]

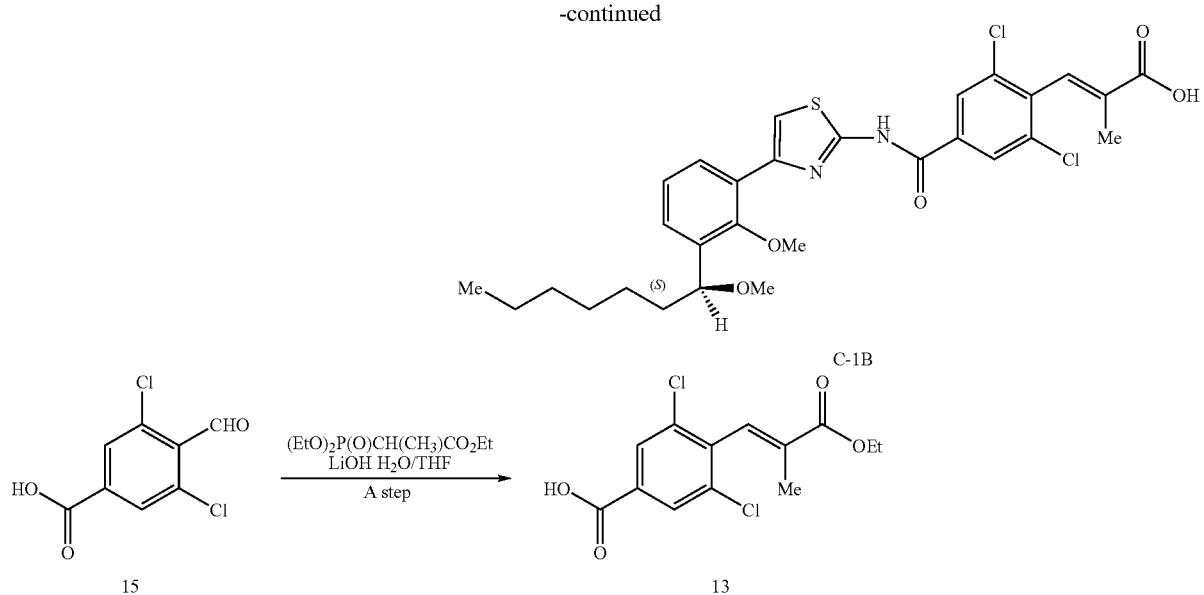

First Step: Synthesis of (S)-1-(3-bromo-2-methyloxyphenyl)heptane-1-ol (8)

Under room temperature, a 1M borane THF solution (48 mL) was added to an R-CBS 1M toluene solution (120 mL). 1-(3-Bromo-2-methyloxyphenyl)heptane-1-one (7, 13 g) was added, and the mixture was stirred for 1 hour. Methanol was added, a solvent was distilled off, and the residue was purified by chromatography to obtain (S)-1-(3-bromo-2-methyloxyphenyl)heptane-1-ol (8, 12.86 g, yield 75%).

Optical rotation: −22.7±0.6 degrees (CHCl$_3$, c=1.008, 21° C.)

NMR (CDCl$_3$) δ ppm: 0.87 (3H, t, J=6.8 Hz), 1.2-1.6 (8H, m), 1.74 (2H, m), 2.09 (1H, brs), 3.88 (3H, s), 4.97 (1H, m), 7.01 (1H, t, J=7.8 Hz), 7.37 (1H, dd, J=7.9 Hz, J=1.3 Hz), 7.46 (1H, dd, J=7.9 Hz, J=1.7 Hz)

Second Step: Synthesis of (S)-1-bromo-2-methyloxy-3-(1-methyloxyheptyl)benzene (9)

(S)-1-(3-bromo-2-methyloxyphenyl)heptanes-1-ol (8, 10 g) obtained in the first step was dissolved in DMSO (42.1 mL), a 50% KOH aqueous solution (4.21 mL), and methane iodide (3.1 mL) were added, and the mixture was stirred for 4 hours. The reaction solution was extracted with isopropyl ether, and purified by silica gel chromatography to obtain (S)-1-bromo-2-methyloxy-3-(1-methyloxyheptyl)benzene (9, 8.77 g, 83%).

Optical rotation: −70.2±0.9 degrees (CHCl$_3$, c=1.050, 21° C.)

NMR (CDCl$_3$) δ ppm: 0.87 (3H, t, J=6.8 Hz), 1.2-1.5 (8H, m), 1.5-1.8 (2H, m), 3.22 (3H, s), 3.85 (3H, s), 4.51 (1H, m), 7.02 (1H, t, J=7.8 Hz), 7.33 (1H, dd, J=7.8 Hz, J=1.7 Hz), 7.46 (1H, dd, J=7.9 Hz, J=1.7 Hz)

Third Step: Synthesis of (S)-2-chloro-1-(2-methyloxy-3-(1-methyloxyheptyl)phenyl)ethanone (11)

To a THF solution of (S)-1-bromo-2-methyloxy-3-(1-methyloxyheptyl)benzene (9, 12.5 g) obtained in the second step was added dropwise a 2M isopropyl magnesium chloride THF solution (44 mL) under ice-cooling. After the reaction solution was stirred at 45° C. for 3 hours, N-methyloxy-N-methyl-2-chloroacetamide (10, 3.5 g) was added under ice-cooling, and the mixture was stirred at room temperature for 1 hour. The reaction solution was extracted with ethyl acetate, and purified by silica gel chromatography to obtain (S)-2-chloro-1-(2-methyloxy-3-(1-methyloxyheptyl)phenyl)ethanone (11).

NMR (CDCl$_3$) δ ppm: 0.87 (3H, t, J=6.8 Hz), 1.2-1.82 (10H, m), 3.22 (3H, s), 3.78 (3H, s), 4.53 (1H, m), 4.73 (2H, m), 7.24 (1H, t, J=7.6 Hz), 7.52 (1H, dd, J=7.6 Hz, J=1.8 Hz), 7.60 (1H, dd, J=7.7 Hz, J=1.8 Hz)

Fourth Step: Synthesis of (S)-4-(2-methyloxy-3-(1-methyloxyheptyl)phenyl)thiazole-2-amine (12)

(S)-2-chloro-1-(2-methyloxy-3-(1-methyloxyheptyl)phenyl)ethanone (11) obtained in the third step was dissolved in ethanol (30 mL), thiourea (1.4 g) was added, and the mixture was stirred at 100° C. for 3 hours. Extraction with toluene and purification by silica gel chromatography afforded (S)-4-(2-methyloxy-3-(1-methyloxyheptyl)phenyl)thiazole-2-amine (12, 4.22 g, yield 32%).

Optical rotation: −54.8±0.9 degrees (DMSO, c=1.045, 21° C.)

NMR (DMSO-d$_6$) δ ppm: 0.84 (3H, t, J=6.5 Hz), 1.2-1.5 (8H, m), 1.5-1.8 (2H, m), 3.13 (3H, s), 3.62 (3H, s), 4.54 (1H, m), 6.99 (2H, brs), 7.05 (1H, s), 7.16 (1H, t, J=7.6 Hz), 7.22 (1H, dd, J=7.5 Hz, J=2.0 Hz), 7.81 (1H, dd, J=7.4 Hz, J=2.0 Hz)

Results of powder X-ray diffraction are shown in FIG. 1 and Table.

TABLE 1

| 2θ | d value | intensity | relative intensity |
|---|---|---|---|
| 10.332 | 8.55452 | 59.8 | 50.4 |
| 10.843 | 8.1527 | 22.5 | 18.9 |
| 11.371 | 7.77554 | 11 | 9.2 |
| 12.042 | 7.34333 | 21.4 | 18.1 |
| 12.635 | 7 | 7.7 | 6.5 |
| 14.094 | 6.27838 | 30.1 | 25.3 |

TABLE 1-continued

| 2θ | d value | intensity | relative intensity |
|---|---|---|---|
| 14.439 | 6.12951 | 10.7 | 9 |
| 16.016 | 5.52906 | 7.21 | 6.1 |
| 16.386 | 5.40521 | 15.8 | 13.3 |
| 16.888 | 5.24555 | 24.3 | 20.5 |
| 17.665 | 5.01658 | 41.2 | 34.7 |
| 18.209 | 4.86789 | 34.2 | 28.8 |
| 18.515 | 4.78822 | 119 | 100 |
| 19.729 | 4.49608 | 12 | 10.1 |
| 20.773 | 4.27259 | 12.3 | 10.3 |
| 21.249 | 4.17792 | 10.3 | 8.6 |
| 21.697 | 4.09268 | 33.2 | 28 |
| 22.049 | 4.02813 | 13.2 | 11.1 |
| 22.734 | 3.90828 | 34.5 | 29 |
| 23.107 | 3.84595 | 103 | 87.1 |
| 23.775 | 3.73934 | 22.9 | 19.3 |
| 24.125 | 3.68592 | 18.2 | 15.3 |
| 24.78 | 3.58996 | 15.1 | 12.7 |
| 25.222 | 3.52804 | 12.9 | 10.9 |
| 25.44 | 3.4983 | 10.9 | 9.2 |
| 26.026 | 3.42082 | 16.6 | 14 |
| 26.761 | 3.3285 | 7.58 | 6.4 |
| 27.268 | 3.26785 | 17.9 | 15 |
| 27.802 | 3.20621 | 8.34 | 7 |
| 28.719 | 3.10589 | 10.3 | 8.6 |
| 30.86 | 2.89516 | 5.89 | 5 |
| 32.688 | 2.73725 | 6.74 | 5.7 |
| 34.001 | 2.63449 | 7.14 | 6 |
| 34.988 | 2.5624 | 6.58 | 5.5 |
| 35.352 | 2.53689 | 5.72 | 4.8 |
| 36.223 | 2.47782 | 5.94 | 5 |
| 37.466 | 2.39845 | 8.53 | 7.2 |
| 38.218 | 2.35294 | 15.8 | 13.3 |
| 39.065 | 2.30387 | 5.44 | 4.6 |
| 39.546 | 2.27693 | 6.48 | 5.5 |

Diffraction angle of main peak: 2θ = 10.33, 17.7, 18.2, 18.5, and 23.1 degrees

Fifth Step: Synthesis of ethyl (S)-(E)-3-(2,6-dichloro-4-(4-(2-methyloxy-3-(1-methyloxyheptyl) phenyl)thiazol-2-ylcarbamoyl)phenyl)-2-methylacrylate (14)

ethyl 3-(4-carboxy-2,6-dichlorophenyl)-2-methylacrylate (13, 3.82 g) obtained in the following A step was dissolved in ethyl acetate (40 mL), diphenoxyphosphoric acid chloride (3 g), and triethylamine (4.2 mL) were added, and (S)-4-(2-methyloxy-3-(1-methyloxyheptyl)phenyl)thiazole-2-amine (12, 4 g) obtained in the third step was added, and the mixture was stirred at room temperature for 6 hours. The reaction solution was extracted with ethyl acetate and, after purification of silica gel chromatography, ethyl (S)-(E)-3-(2,6-dichloro-4-(4-(2-methyloxy-3-(1-methyloxyheptyl)phenyl) thi-azol-2-ylcarbamoyl)phenyl)-2-methylacrylate (14, 7.0 g, yield 95%) was obtained.

Optical rotation: −24.1±0.6 degrees (CHCl$_3$, c=1.040, 21° C.)

NMR (CDCl$_3$) δ ppm: 0.88 (3H, t, J=6.5 Hz), 1.2-1.8 (10H, m), 1.37 (3H, t, J=7.1 Hz), 1.77 (3H, d, J=1.4 Hz), 3.23 (3H, s), 3.59 (3H, s), 4.31 (2H, q, J=7.1 Hz), 4.56 (1H, m), 7.15 (1H, t, J=7.6 Hz), 7.35 (1H, dd, J=7.6 Hz, J=1.7 Hz), 7.41 (1H, d, J=1.2 Hz), 7.52 (1H, s), 7.67 (1H, dd, J=7.6 Hz, J=1.7 Hz), 7.88 (2H, s), 10.42 (1H, brs)

Sixth Step: Synthesis of (S)-(E)-3-(2,6-dichloro-4-(4-(2-methyloxy-3-(1-methyloxyheptyl)phenyl)thiazol-2-ylcarbamoyl)phenyl)-2-methylacrylic acid (C-1B)

Ethyl (S)-(E)-3-(2,6-dichloro-4-(4-(2-methyloxy-3-(1-methyloxyheptyl)phenyl)thiazol-2-ylcarbamoyl)phenyl)-2-methylacrylate (14, 6.76 g) obtained in the fifth step was dissolved in THF (20 mL) and ethanol (20 mL), a 4 mol/L sodium hydroxide aqueous solution (13.5 mL) was added, and the mixture was stirred at room temperature for 2 hours. The reaction solution was neutralized with hydrochloric acid, and extracted with ethyl acetate. The extraction residue was recrystallized with methanol to obtain (S)-(E)-3-(2,6-dichloro-4-(4-(2-methyloxy-3-(1-methyloxyheptyl)phenyl) thiazol-2-ylcarbamoyl)phenyl)-2-methylacrylic acid (C-1B, 5.8 g, yield 88%).

Optical rotation: −33.3±0.6 degrees (CHCl$_3$, c=1.067, 21° C.)

NMR (CDCl$_3$) δ ppm: 0.86 (3H, t, J=6.7 Hz), 1.22-1.82 (10H, m), 1.86 (3H, d, J=1.2 Hz), 3.27 (3H, s), 3.54 (3H, s), 4.61 (1H, m), 7.25 (1H, t, J=7.8 Hz), 7.41 (1H, s), 7.43 (1H, dd, J=7.9 Hz, J=1.8 Hz), 7.52 (1H, dd, J=7.5 Hz, J=1.7 Hz), 7.41 (1H, d, J=1.4 Hz), 8.32 (2H, s), 13.3 (2H, brs)

Results of powder X-ray deffraction are shown in FIG. 2.

Deffraction angle of main peak 2θ=4.2, 6.4, 12.3, 13.2, 23.6, 23.8, and 24.7 degrees A Step: Synthesis of ethyl 3-(4-carboxy-2,6-dichlorophenyl)-2-methylacrylate (13)

Triethylphosphonopropionate (4.5 g) was dissolved in THF (15 mL), sodium hydride (1.59 g) was added under ice-cooling, and the mixture was stirred for 30 minutes. To the solution was added a solution obtained by dissolving 3,5-dichloro-4-formyl-benzoic acid (3.9 g) in THF (10 mL), and the mixture was further stirred for 1 hour and 20 minutes. The reaction solution was extracted with ethyl acetate, and a solvent was distilled off until a weight including a weight of the solvent became 11.7 g. The precipitated crystal was filtered off, and washed with a mixed solvent of ethyl acetate and n-heptane (1:2) to obtain ethyl 3-(4-carboxy-2,6-dichlorophenyl)-2-methylacrylate (13, 3.98 g).

Melting point: 145° C.

NMR (CDCl$_3$) δ ppm: 8.07 (s, 2H), 7.47 (s, 1H), 4.32 (q, 2H, J=7.0 Hz), 1.79 (s, 3H), 1.38 (t, 3H, J=7.0 Hz)

Results of powder X-ray deffraction are shown in FIG. 3.

TABLE 2

| 2θ | d value | intensity | relative intensity |
|---|---|---|---|
| 8.108 | 10.8953 | 56.3 | 44.3 |
| 10.78 | 8.20055 | 6.2 | 4.9 |
| 16.257 | 5.44785 | 127 | 100 |
| 19.185 | 4.62239 | 18.4 | 14.5 |
| 19.968 | 4.44294 | 23.9 | 18.8 |
| 22.076 | 4.02312 | 4.88 | 3.8 |
| 24.463 | 3.63573 | 12.9 | 10.2 |
| 24.801 | 3.58703 | 30.1 | 23.7 |
| 26.232 | 3.39442 | 15.5 | 12.2 |
| 26.63 | 3.34461 | 6.88 | 5.4 |
| 27.294 | 3.26469 | 8.86 | 7 |
| 27.871 | 3.19848 | 4.55 | 3.6 |
| 30.918 | 2.88984 | 5.05 | 4 |
| 31.317 | 2.85387 | 10.5 | 8.3 |
| 32.152 | 2.78163 | 10.3 | 8.1 |
| 32.84 | 2.72495 | 15.6 | 12.3 |
| 34.166 | 2.62214 | 3.55 | 2.8 |
| 35.122 | 2.55297 | 12.8 | 10.1 |
| 36.042 | 2.48989 | 4.74 | 3.7 |
| 37.931 | 2.37008 | 13.1 | 10.3 |
| 38.508 | 2.33593 | 5.61 | 4.4 |
| 39.028 | 2.30595 | 25 | 19.7 |

Diffraction angle of main peak: 2θ = 8.1, 16.3, 19.2, 20.0, 24.8, and 39.0 degrees

Example 4

Synthesis of (C-3B)

[Chemical formula 17]

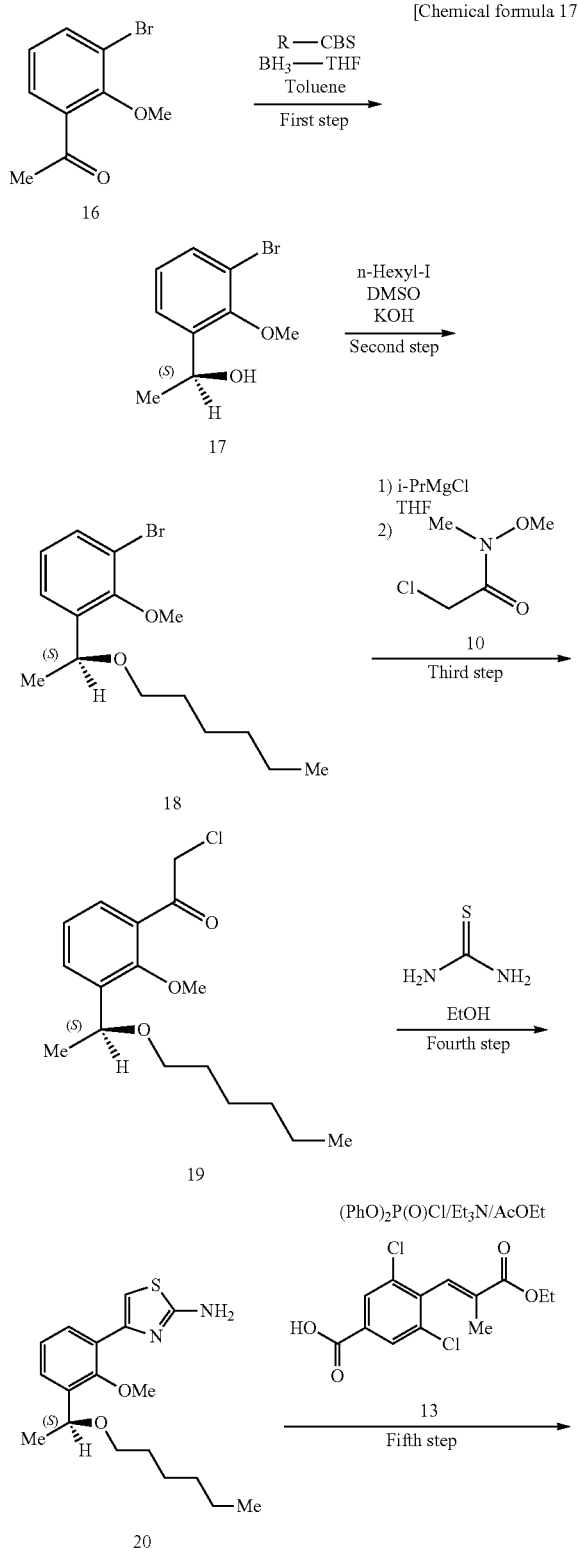

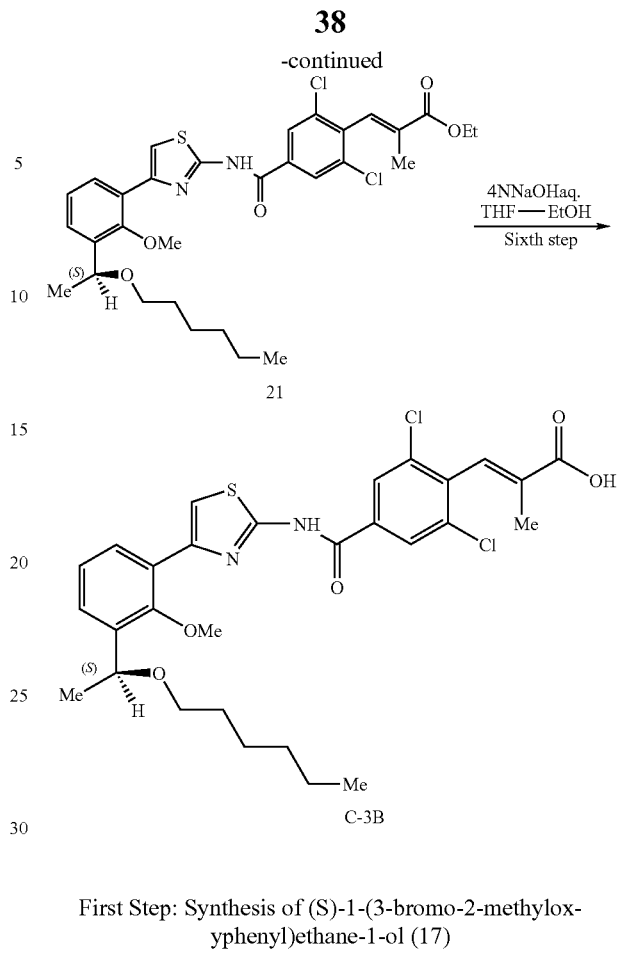

First Step: Synthesis of (S)-1-(3-bromo-2-methyloxyphenyl)ethane-1-ol (17)

Using the same method as that of the first step of Example 3, the compound (17) was obtained from the compound (16) at a yield 77%.

Optical rotation: −23.5±0.6 degrees (CHCl$_3$, c=1.050, 21° C.)

NMR (CDCl$_3$) δ ppm: 1.49 (3H, d, J=6.6 Hz), 2.33 (1H, brs), 3.88 (3H, s), 5.19 (1H, q, J=6.4 Hz), 7.01 (1H, t, J=7.9 Hz), 7.40 (1H, dd, J=7.7 Hz, J=1.1 Hz), 7.46 (1H, dd, J=8.0 Hz, J=1.4 Hz)

Second Step: Synthesis of (S)-1-bromo-3-(1-hexyloxyethyl)-2-methyloxybenzene (18)

Using the same method as that of the second step of Example 3, the compound (18) was obtained from the compound (17) at a yield of 96%.

Optical rotation: −29.8±0.6 degrees (CHCl$_3$, c=1.055, 21° C.)

NMR (CDCl$_3$) δ ppm: 0.87 (3H, t, J=6.8 Hz), 1.2-1.4 (6H, m), 1.42 (3H, d, J=6.5 Hz), 1.54 (2H, m), 3.29 (2H, m), 3.85 (3H, s), 4.78 (1H, q, J=6.4 Hz), 7.02 (1H, t, J=7.9 Hz), 7.39 (1H, dd, J=7.8 Hz, J=1.7 Hz), 7.45 (1H, dd, J=7.9 Hz, J=1.7 Hz)

Third Step and Fourth Step: Synthesis of (S)-4-(3-(1-hexyloxyethyl)-2-methyloxyphenyl)thiazole-2-amine (20)

Using the same method as that of the fourth step of Example 3, the compound (19) was obtained from the compound (18), subsequently according to the same method as that of the fourth step, the compound (20) was obtained.

Compound (19)

NMR (CDCl$_3$) δ ppm: 0.87 (3H, t, J=6.9 Hz), 1.2-1.4 (6H, m), 1.45 (3H, d, J=6.6 Hz), 1.55 (2H, m), 3.29 (2H, m), 3.78 (3H, s), 4.73 (2H, m), 4.80 (1H, q, J=6.4 Hz), 7.24 (1H, t, J=7.8 Hz), 7.52 (1H, dd, J=7.7 Hz, J=1.8 Hz), 7.65 (1H, dd, J=7.7 Hz, J=1.8 Hz)

Compound (20)

Optical rotation: −4.2±0.4 degrees (DMSO, c=1.025, 21° C.)

NMR (CDCl$_3$) δ ppm: 0.84 (3H, t, J=7.0 Hz), 1.2-1.3 (6H, m), 1.35 (3H, d, J=6.5 Hz), 1.48 (2H, m), 3.25 (2H, m), 3.61 (3H, s), 4.78 (1H, q, J=6.4 Hz), 6.99 (2H, brs), 7.05 (1H, s), 7.16 (1H, t, J=7.7 Hz), 7.27 (1H, dd, J=7.5 Hz, J=1.8 Hz), 7.81 (1H, dd, J=7.6 Hz, J=1.9 Hz)

Results of powder X-ray deffraction are shown in FIG. 4.

TABLE 3

| 2θ | d value | intensity | relative intensity |
|---|---|---|---|
| 8.173 | 10.80873 | 22 | 6.3 |
| 10.15 | 8.70733 | 7.99 | 2.3 |
| 12.044 | 7.34226 | 10.3 | 2.9 |
| 12.526 | 7.06085 | 29.7 | 8.5 |
| 12.96 | 6.82519 | 25.5 | 7.3 |
| 13.633 | 6.48972 | 30.2 | 8.6 |
| 15.455 | 5.72849 | 22.7 | 6.5 |
| 16.399 | 5.401 | 350 | 100 |
| 16.74 | 5.29166 | 32.3 | 9.2 |
| 17.319 | 5.1161 | 6.26 | 1.8 |
| 17.734 | 4.99722 | 6.53 | 1.9 |
| 18.352 | 4.83027 | 14.1 | 4 |
| 19.025 | 4.66083 | 12 | 3.4 |
| 19.875 | 4.46344 | 20.1 | 5.8 |
| 21.323 | 4.1635 | 9.66 | 2.8 |
| 21.65 | 4.10143 | 12.7 | 3.6 |
| 23.026 | 3.85932 | 47.5 | 13.6 |
| 23.32 | 3.81131 | 18.6 | 5.3 |
| 24.265 | 3.66492 | 56.2 | 16.1 |
| 24.56 | 3.62162 | 24.8 | 7.1 |
| 24.944 | 3.56676 | 9.41 | 2.7 |
| 25.234 | 3.52635 | 7.91 | 2.3 |
| 25.556 | 3.48265 | 8.01 | 2.3 |
| 26.107 | 3.41041 | 16.8 | 4.8 |
| 26.453 | 3.36656 | 26.6 | 7.6 |
| 27.523 | 3.23813 | 9.86 | 2.8 |
| 28.638 | 3.11453 | 5.91 | 1.7 |
| 29.371 | 3.03844 | 5.3 | 1.5 |
| 30.268 | 2.95039 | 5.29 | 1.5 |
| 30.78 | 2.90248 | 6.06 | 1.7 |
| 32.347 | 2.76539 | 7.26 | 2.1 |
| 33.111 | 2.70324 | 5.69 | 1.6 |
| 33.774 | 2.65169 | 15.2 | 4.4 |
| 35.952 | 2.49588 | 14 | 4 |
| 36.615 | 2.45222 | 9.01 | 2.6 |

TABLE 3-continued

| 2θ | d value | intensity | relative intensity |
|---|---|---|---|
| 36.905 | 2.43363 | 11.2 | 3.2 |
| 38.207 | 2.35362 | 13.7 | 3.9 |
| 38.784 | 2.31991 | 7.98 | 2.3 |

Diffraction angle of main peak: 2θ = 12.5, 13.0, 13.6, 16.4, 23.0, and 24.3 degrees Fifth Step: Synthesis of ethyl (S)-(E)-3-(2,6-dichloro-4-(4-(3-(1-hexyloxyethyl)-2-methyloxyphenyl)thiazol-2-ylcarbamoyl)phenyl)-2-methylacrylate (21)

Using the same method as that of the fifth step of Example 3, the compound (21) was obtained from the compound (20) at a yield of 94%.

Optical rotation: +4.7±0.4 degrees (CHCl$_3$, c=1.07, 21° C.)
NMR (CDCl$_3$) δ ppm: 0.87 (3H, t, J=6.9 Hz), 1.2-1.35 (6H, m), 1.38 (3H, t, J=7.1 Hz), 1.44 (3H, d, J=6.4 Hz), 1.57 (2H, m), 1.77 (3H, d, J=1.4 Hz), 3.30 (2H, m), 3.59 (3H, s), 4.31 (2H, q, J=7.1 Hz), 4.83 (1H, q, J=6.4 Hz), 7.17 (1H, t, J=7.7 Hz), 7.42 (1H, d, J=1.7 Hz), 7.42 (1H, dd, J=7.7 Hz, J=1.8 Hz), 7.51 (1H, s), 7.67 (1H, dd, J=7.6 Hz, J=1.7 Hz), 7.89 (2H, s), 10.30 (1H, brs)

Sixth Step: Synthesis of (S)-(E)-3-(2,6-dichloro-4-(4-(3-(1-hexyloxyethyl)-2-methyloxyphenyl)thiazol-2-ylcarbamoyl)phenyl)-2-methylacrylic acid (C-3B)

Using the same method as that of the sixth step of Example 3, the compound (C-3B) was obtained from the compound (21) at a yield of 80%.

Optical rotation: −7.0±0.5 degrees (CHCl$_3$, c=1.040, 21° C.)
NMR (CDCl$_3$) δ ppm: 0.87 (3H, t, J=6.8 Hz), 1.2-1.4 (6H, m), 1.48 (3H, d, J=6.4 Hz), 1.52-1.64 (2H, m), 1.86 (3H, d, J=1.4 Hz), 3.35 (2H, t, J=6.7 Hz), 3.55 (3H, s), 4.87 (1H, q, J=6.3 Hz), 7.25 (1H, t, J=7.7 Hz), 7.41 (1H, s), 7.49 (1H, dd, J=7.9 Hz, J=1.6 Hz), 7.51 (1H, dd, J=7.5 Hz, J=1.8 Hz), 7.65 (1H, d, J=1.4 Hz), 8.33 (2H, s), 13.4 (2H, brs)

Results of powder X-ray deffraction are shown in FIG. 5.
Diffraction angle of main peak: 2θ=17.8, 21.1, 22.5, 23.3, 24.1, and 24.4 degrees Example 5

Synthesis of (C-9B)

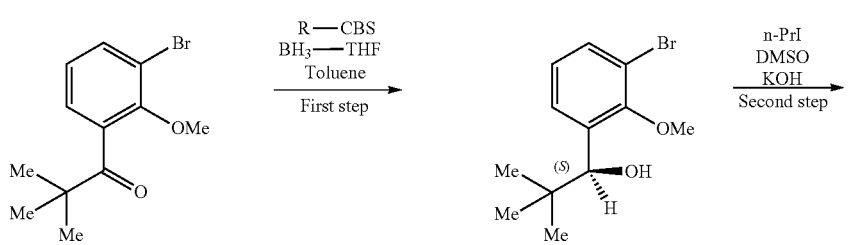

[Chemical formula 18]

-continued
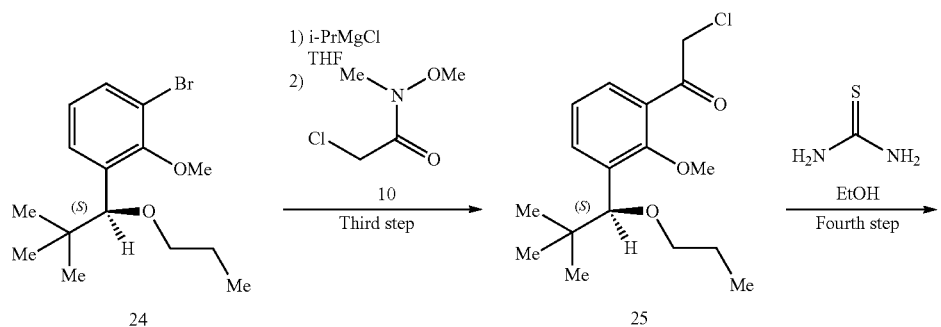
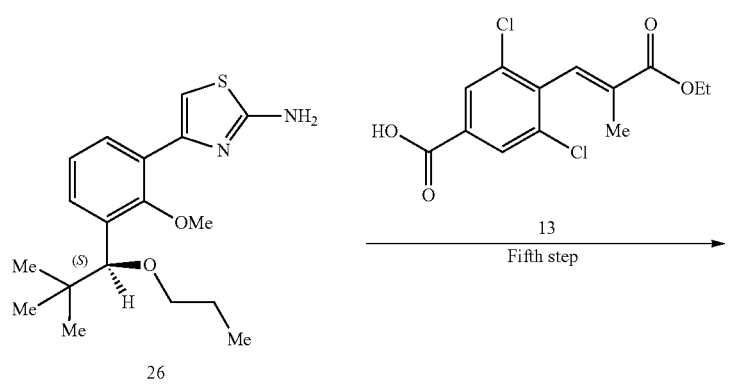
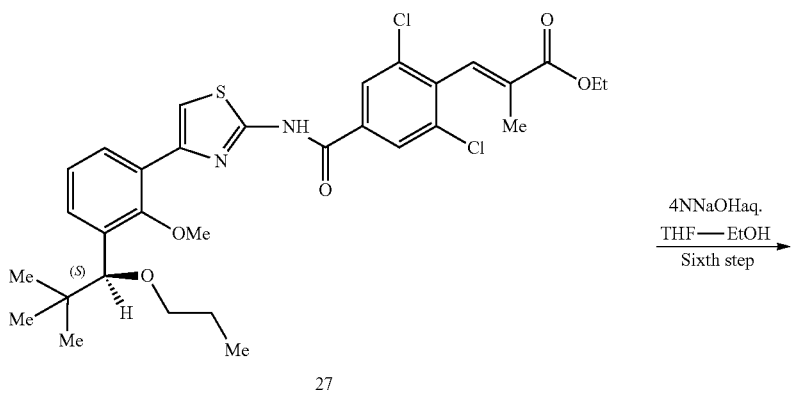
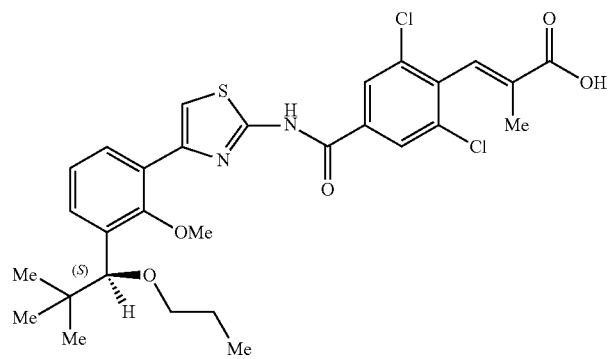

First Step: Synthesis of (S)-1-(3-bromo-2-methyloxyphenyl)-2,2-dimethyl-propyl-1-ol (23)

Using the same method as that of the first step of Example 3, the compound (23) was obtained from the compound (22) at a yield of 86%.
Optical rotation: −6.1±0.4 degrees (CHCl₃, c=1.070, 21° C.)
NMR (CDCl₃) δ ppm: 0.92 (9H, s), 2.06 (1H, brs), 3.83 (3H, s), 4.78 (1H, s), 6.99 (1H, t, J=7.8 Hz), 7.38 (1H, dd, J=7.8 Hz, J=1.6 Hz), 7.46 (1H, dd, J=7.9 Hz, J=1.7 Hz)

Second Step: Synthesis of (S)-1-bromo-3-(2,2-dimethyl-1-propyloxypropyl)-2-methyloxybenzene (24)

Using the same method as that of the second step of Example 3, the compound (24) was obtained from the compound (23) at a yield of 84%.
: +3.2±0.4 degrees (CHCl₃, c=1.080, 21° C.)
NMR (CDCl₃) δ ppm: 0.89 (9H, s), 0.92 (3H, t, J=7.2 Hz), 1.56 (2H, m), 3.19 (2H, 3.83 (3H, s), 4.30 (1H, s), 6.98 (1H, t, J=7.9 Hz), 7.34 (1H, dd, J=7.9 Hz, J=1.6 Hz), 7.45 (1H, dd, J=7.8 Hz, J=1.6 Hz)

Third Step and Forth Step: Synthesis of (S)-4-(3-(2,2-dimethyl-1-propyloxypropyl)-2-methyloxyphenyl)thiazole-2-amine (26)

Using the same method as that of the third step of Example 3, the compound (25) was obtained from the compound (24), and subsequently according to the same method as that of the fourth step, the compound (26) was obtained.
Compound (25)
NMR (CDCl₃) δ ppm: 0.90 (9H, s), 0.92 (3H, t, J=7.2 Hz), 1.57 (2H, m), 3.19 (2H, m), 3.74 (3H, s), 4.32 (1H, s), 4.71 (2H, m), 7.21 (1H, t, J=7.7 Hz), 7.49 (1H, dd, J=7.7 Hz, J=1.8 Hz), 7.61 (1H, dd, J=7.7 Hz, J=1.7 Hz)
Compound (26)
Optical rotation: −93.6±1.2 degrees (DMSO, c=1.070, 21° C.)
NMR (CDCl₃) δ ppm: 0.87 (9H, s), 0.89 (3H, t, J=7.4 Hz), 1.52 (2H, m), 3.19 (2H, m), 3.58 (3H, s), 4.37 (1H, s), 6.99 (2H, brs), 7.02 (1H, s), 7.14 (1H, t, J=7.7 Hz), 7.21 (1H, dd, J=7.6 Hz, J=2.1 Hz), 7.80 (1H, dd, J=7.4 Hz, J=2.0 Hz)

Fifth Step: Synthesis of ethyl (S)-(E)-3-(2,6-dichloro-4-(4-(3-(2,2-dimethyl-1-propyloxypropyl)-2-methyloxyphenyl)thiazol-2-ylcarbamoyl)phenyl)-2-methylacrylate (27)

Using the same method as that of the fifth step of Example 3, the compound (27) was obtained from the compound (26) at a yield of 94%.
Optical rotation: −79.5±1.2 degrees (CHCl₃, c=1.010, 21° C.)
NMR (CDCl₃) δ ppm: 0.89 (9H, s), 0.92 (3H, t, J=7.2 Hz), 1.37 (3H, t, J=7.1 Hz), 1.56 (2H, m), 1.76 (3H, d, J=1.5 Hz), 3.18 (2H, m), 3.53 (3H, s), 4.31 (2H, q, J=7.1 Hz), 4.32 (1H, s), 7.08 (1H, t, J=7.6 Hz), 7.34 (1H, dd, J=7.7 Hz, J=1.8 Hz), 7.40 (1H, d, J=1.4 Hz), 7.51 (1H, s), 7.62 (1H, dd, J=7.6 Hz, J=1.8 Hz), 7.84 (2H, s), 10.77 (1H, brs)

Sixth Step: Synthesis of (S)-(E)-3-(2,6-dichloro-4-(4-(3-(2,2-dimethyl-1-propyloxypropyl)-2-methyloxy)phenyl)thiazol-2-ylcarbamoyl)phenyl)-2-methylacrylic acid (C-9B)

Using the same method as that of the sixth step of Example 3, the compound (C-9B) was obtained from the compound (27) at a yield of 87%.

Optical rotation: −61.6±0.9 degrees (CHCl₃, c=1.018, 21° C.)
NMR (CDCl₃) δ ppm: 0.90 (9H, s), 0.90 (3H, t, J=7.4 Hz), 1.53 (2H, m), 1.69 (3H, d, J=1.1 Hz), 3.21 (2H, m), 3.57 (3H, s), 4.40 (1H, s), 7.24 (1H, t, J=7.6 Hz), 7.29 (1H, dd, J=7.7 Hz, J=2.1 Hz), 7.40 (1H, d, J=1.4 Hz), 7.68 (1H, s), 7.89 (1H, dd, J=7.4 Hz, J=2.1 Hz), 8.28 (2H, s), 12.98 (2H, brs)

Results of powder X-ray diffraction are shown in FIG. 6.
Diffraction angle of main peak: 2θ=13.6, 16.1, 21.2, 23.4, and 24.5 degrees Using the same methods as those of Examples 1 to 5, the following optically active compounds can be synthesized.

TABLE 4

| Compound No. | Compound name |
|---|---|
| C-2A | (R)-(E)-3-(2,6-dichloro-4-{4-[2-methyloxy-3-(1-pentyloxyethyl)phenyl]thiazol-2-ylcarbamoyl}phenyl)-2-methylacrylic acid |
| C-2B | (S)-(E)-3-(2,6-dichloro-4-{4-[2-methyloxy-3-(1-pentyloxyethyl)phenyl]thiazol-2-ylcarbamoyl}phenyl)-2-methylacrylic acid |
| C-4A | (R)-(E)-3-(2,6-dichloro-4-{4-[2-methyloxy-3-(1-methyloxyhexyl)phenyl]thiazol-2-ylcarbamoyl}phenyl)-2-methylacrylic acid |
| C-4B | (S)-(E)-3-(2,6-dichloro-4-{4-[2-methyloxy-3-(1-methyloxyhexyl)phenyl]thiazol-2-ylcarbamoyl}phenyl)-2-methylacrylic acid |
| C-5A | (R)-(E)-3-(2,6-dichloro-4-{4-[3-(1-ethyloxyhexyl)-2-methyloxyphenyl]thiazol-2-ylcarbamoyl}phenyl)-2-methylacrylic acid |
| C-5B | (S)-(E)-3-(2,6-dichloro-4-{4-[3-(1-ethyloxyhexyl)-2-methyloxyphenyl]thiazol-2-ylcarbamoyl}phenyl)-2-methylacrylic acid |
| C-6A | (R)-(E)-3-(2,6-dichloro-4-{4-[3-(1-ethyloxypentyl)-2-methyloxyphenyl]thiazol-2-ylcarbamoyl}phenyl)-2-methylacrylic acid |
| C-6B | (S)-(E)-3-(2,6-dichloro-4-{4-[3-(1-ethyloxypentyl)-2-methyloxyphenyl]thiazol-2-ylcarbamoyl}phenyl)-2-methylacrylic acid |
| C-7A | (R)-(E)-3-(2,6-dichloro-4-{4-[2-methyloxy-3-(1-propyloxypentyl)phenyl]thiazol-2-ylcarbamoyl}phenyl)-2-methylacrylic acid |
| C-7B | (S)-(E)-3-(2,6-dichloro-4-{4-[2-methyloxy-3-(1-propyloxypentyl)phenyl]thiazol-2-ylcarbamoyl}phenyl)-2-methylacrylic acid |
| C-8A | (R)-(E)-3-(2,6-dichloro-4-{4-[3-(2,2-dimethylpropyl-1-ethyloxy)-2-methyloxyphenyl]thiazol-2-ylcarbamoyl}phenyl)-2-methylacrylic acid |
| C-8B | (S)-(E)-3-(2,6-dichloro-4-{4-[3-(2,2-dimethylpropyl-1-ethyloxy)-2-methyloxyphenyl]thiazol-2-ylcarbamoyl}phenyl)-2-methylacrylic acid |
| C-9B | (S)-(E)-3-(2,6-dichloro-4-{4-[3-(2,2-dimethyl-1-propyloxypropyl)-2-methyloxyphenyl]thiazol-2-ylcarbamoyl}phenyl)-2-methylacrylic acid |
| C-10A | (R)-(E)-3-(2,6-dichloro-4-{4-[2-methyloxy-3-(1-propyloxybutyl)phenyl]thiazol-2-ylcarbamoyl}phenyl)-2-methylacrylic acid |
| C-10B | (S)-(E)-3-(2,6-dichloro-4-{4-[2-methyloxy-3-(1-propyloxybutyl)phenyl]thiazol-2-ylcarbamoyl}phenyl)-2-methylacrylic acid |

TABLE 5

| Compound No. | Compound name |
|---|---|
| C-11A | (R)-(E)-3-(4-{4-[3-(1-butyloxybutyl)-2-methyloxyphenyl]thiazol-2-ylcarbamoyl}-2,6-dichlorophenyl)-2-methylacrylic acid |
| C-11B | (S)-(E)-3-(4-{4-[3-(1-butyloxybutyl)-2-methyloxyphenyl]thiazol-2-ylcarbamoyl}-2,6-dichlorophenyl)-2-methylacrylic acid |

TABLE 5-continued

| Compound No. | Compound name |
|---|---|
| C-12A | (R)-(E)-3-(2,6-dichloro-4-{4-[3-(1-ethyloxy-3-methylbutyl)-2-methyloxyphenyl]thiazol-2-ylcarbamoyl}phenyl)-2-methylacrylic acid |
| C-12B | (S)-(E)-3-(2,6-dichloro-4-{4-[3-(1-ethyloxy-3-methylbutyl)-2-methyloxyphenyl]thiazol-2-ylcarbamoyl}phenyl)-2-methylacrylic acid |
| C-13A | (R)-(E)-3-(2,6-dichloro-4-{4-[2-methyloxy-3-(2-methyl-1-propyloxypropyl)phenyl]thiazol-2-ylcarbamoyl}phenyl)-2-methylacrylic acid |
| C-13B | (S)-(E)-3-(2,6-dichloro-4-{4-[2-methyloxy-3-(2-methyl-1-propyloxypropyl)phenyl]thiazol-2-ylcarbamoyl}phenyl)-2-methylacrylic acid |
| C-14A | (R)-(E)-3-(4-{4-[3-(1-butyloxypropyl)-2-methyloxyphenyl]thiazol-2-ylcarbamoyl}-2,6-dichlorophenyl)-2-methylacrylic acid |
| C-14B | (S)-(E)-3-(4-{4-[3-(1-butyloxypropyl)-2-methyloxyphenyl]thiazol-2-ylcarbamoyl}-2,6-dichlorophenyl)-2-methylacrylic acid |
| C-15A | (R)-(E)-3-(2,6-dichloro-4-{4-[2-methyloxy-3-(1-pentyloxypropyl)phenyl]thiazol-2-ylcarbamoyl}phenyl)-2-methylacrylic acid |
| C-15B | (S)-(E)-3-(2,6-dichloro-4-{4-[2-methyloxy-3-(1-pentyloxypropyl)phenyl]thiazol-2-ylcarbamoyl}phenyl)-2-methylacrylic acid |
| C-16A | (R)-(E)-3-(2,6-dichloro-4-{4-[2-methyloxy-3-(1-methyloxy-5-methylhexyl)phenyl]thiazol-2-ylcarbamoyl}-phenyl)-2-methylacrylic acid |
| C-16B | (S)-(E)-3-(2,6-dichloro-4-{4-[2-methyloxy-3-(1-methyloxy-5-methylhexyl)phenyl]thiazol-2-ylcarbamoyl}-phenyl)-2-methylacrylic acid |

Test Examples

Test Example 1

Isolation and Purification of Thrombopoietin (TPO)

Human and mouse TPOs were purchased from R&D Systems.

Test Example 2

TPO Receptor Responsiveness

TPO receptor responsiveness of the compound represented by the formula (I) was measured using TPO-dependent cell strain BaF/hTPOR made by introducing a human TPO receptor gene into a BaF-B03 cell according to the method described in Collins et al., J. Cell. Physiol., 137: 293-298 (1988). A nucleotide sequence of a gene encoding thrombopoietin receptor is described in Vigon et al., Proc. Natl. Acad. Sci. 89:5640-5644 (1992). TPO does not respond to a BaF-B03 cell which is a parent strain. A BAF/hTPOR cell proliferated in a RPMI medium with 10% WEHI-3 culture solution added thereto was washed with PBS once, suspended in a RPMI medium with no WHEHI-3 culture solution added thereto, and cells were seeded on a 96-well microplate at a $5 \times 10^4$/well, and the present compound or TPO was added thereto. After cultured at 37° C. for 20 hours under 5% $CO_2$ atmosphere, a WST-1 reagent (manufactured by Takara Shuzo, Co., Ltd) being a cell proliferation determination reagent was added, and absorption at 450 nm was measured after 4 hours. An $ED_{50}$ value was defined as a concentration of a compound exhibiting half-maximum responsiveness of human TPO, and an $ED_{50}$ value of each compound is shown in Table 6.

TABLE 6

| Compound N | $ED_{50}$ (nM) |
|---|---|
| C-1A | 3.09 |
| C-1B | 2.08 |
| C-3A | 1.40 |
| C-3B | 1.09 |
| C-9B | 0.09 |

Test Example 3

In Vivo Drug Efficacy Test Using Knock-in Mouse in which a Transmembrane Site of a Mouse TPO Receptor Gene is Substituted with a Human Type The presence or the absence of drug efficacy can be confirmed by continuously orally administering a compound (C-1A), a compound (C-1B), a compound (C-3A), a compound (C-3B), or a compound (C-9B) twice a day for 2 weeks, collecting blood three days, one week, two weeks, and three weeks after initiation of initial administration, and confirming that the platelet number is increased as compared with a Vehicle administration group.

Preparation Example

Preparation Example 1

A granule containing the following components is prepared.

| Component | | |
|---|---|---|
| | Optically active compound represented by the formula (I) | 10 mg |
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 120 mesh sieve. These are mixed with a V-type mixing machine. To a mixed powder is added a HPC-L (low viscosity hydroxypropylcellulose) aqueous solution, this is kneaded, granulated (extrusion granulation, pore diameter 0.5 to 1 mm) and dried. The resulting dry granule is passed through a vibration sieve (12/60 mesh) to obtain a granule.

Preparation Example 2

A capsule filling powder containing the following components is prepared.

| Component | | |
|---|---|---|
| | Optically active compound represented by the formula (I) | 10 mg |
| | Lactose | 79 mg |
| | Corn starch | 10 mg |
| | Magnesium stearate | 1 mg |
| | | 100 mg |

The compound represented by the formula (I) and lactose are passed through a 60 mesh sieve. Corn starch is passed through a 120 sieve. These and magnesium stearate are mixed with a V-type mixing machine. 100 mg of 10 trituration is filled into a No. 5 hard gelatin capsule.

Preparation Example 3

A capsule filing granule containing the following components is prepared.

| Component | | |
|---|---|---|
| | Optically active compound represented by the formula (I) | 15 mg |
| | Lactose | 90 mg |
| | Corn starch | 42 mg |
| | HPC-L | 3 mg |
| | | 150 mg |

The compound represented by the formula (I), and lactose are passed through a 60 mesh sieve. Corn starch is passed through a 120 mesh sieve. These are mixed, a HPC-L solution is added to a mixed powder, and this is kneaded, granulated and dried. The resulting dry granule is adjusted in a particle size, 150 mg of which is filled into a No. 4 hard gelatin capsule.

Preparation Example 4

A tablet containing the following components is prepared.

| Component | | |
|---|---|---|
| | Optically active compound represented by the formula (I) | 10 mg |
| | Lactose | 90 mg |
| | Microcrystalline cellulose | 30 mg |
| | CMC-Na | 15 mg |
| | Magnesium stearate | 5 mg |
| | | 150 mg |

The compound represented by the formula (I), lactose, microcrystalline cellulose and CMC-Na (carboxymethylcellulose sodium salt) are passed through a 60 mesh sieve, and mixed. Magnesium stearate is mixed into a mixed powder to obtain a preparation mixed powder. The present mixed powder is directly compressed to obtain 150 mg of a tablet.

Preparation Example 5

An intravenous preparation is prepared as follows:

| | |
|---|---|
| Optically active compound represented by the formula (I) | 100 mg |
| Saturated fatty acid glyceride | 1000 ml |

A solution of the above components is intravenously administered to a patient at a rate of 1 ml per minute.

INDUSTRIAL APPLICABILITY

It has been found out that the optically active 4-phenylthiazole derivative has the excellent thrombopoietin agonist activity, exhibits a high oral absorbability and/or a high in vivo activity, and a pharmaceutical composition containing the compound as an active ingredient is effective as a therapeutic and/or a preventive of a blood disease accompanied with an abnormality of the blood platelet number such as thrombocytopenia or the like. In addition, it has been found out that the crystal has a high stability and/or a high purity, and an intermediate has a high stability, and they are useful in preparation of a 4-phenylthiazole derivative and/or preparation of a pharmaceutical composition.

Figure 1:
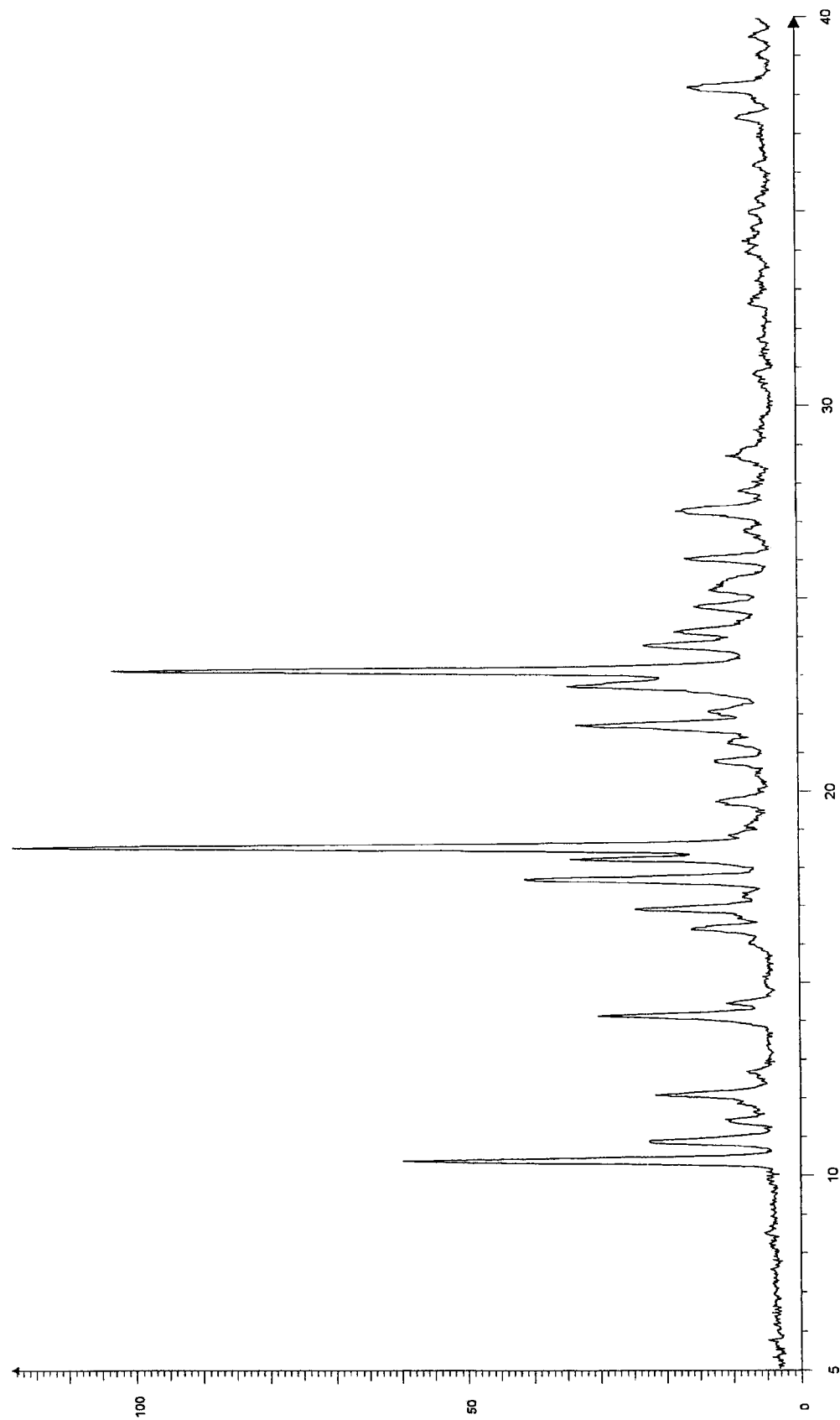
[FIG. 1] A powder X-ray diffraction pattern and a peak value thereof of the compound (12) crystal obtained in the fourth step of Example 3. An ordinate axis indicates an intensity and an abscissa axis indicates a diffraction angle (2θ, unit: degree).
Figure 2:
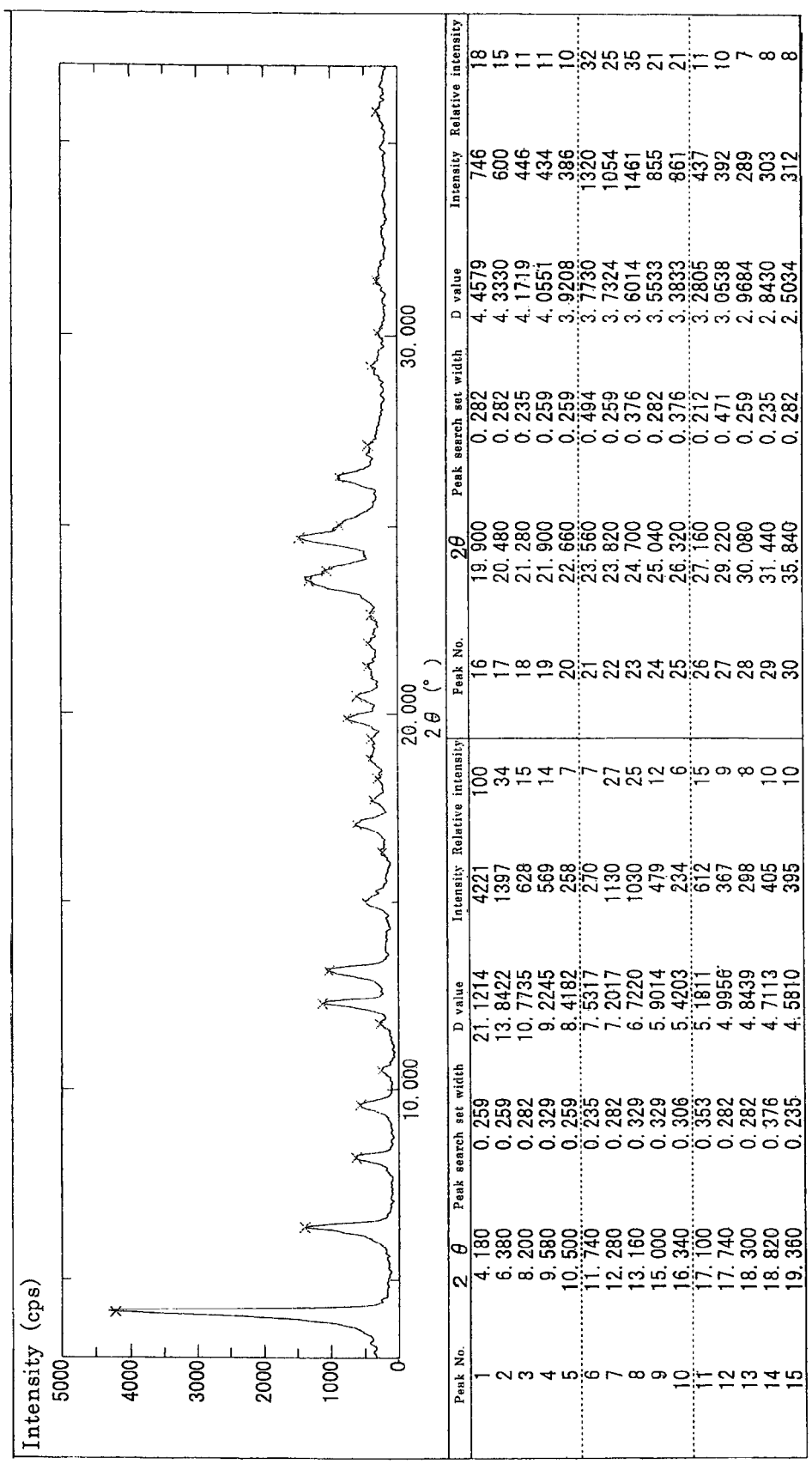
[FIG. 2] A powder X-ray diffraction pattern and a peak value thereof of the compound (C-1B) crystal obtained in the sixth step of Example 3. An ordinate axis indicates an intensity (unit: cps) and an abscissa axis indicates a diffraction angle (2θ, unit: degree).
Figure 3:
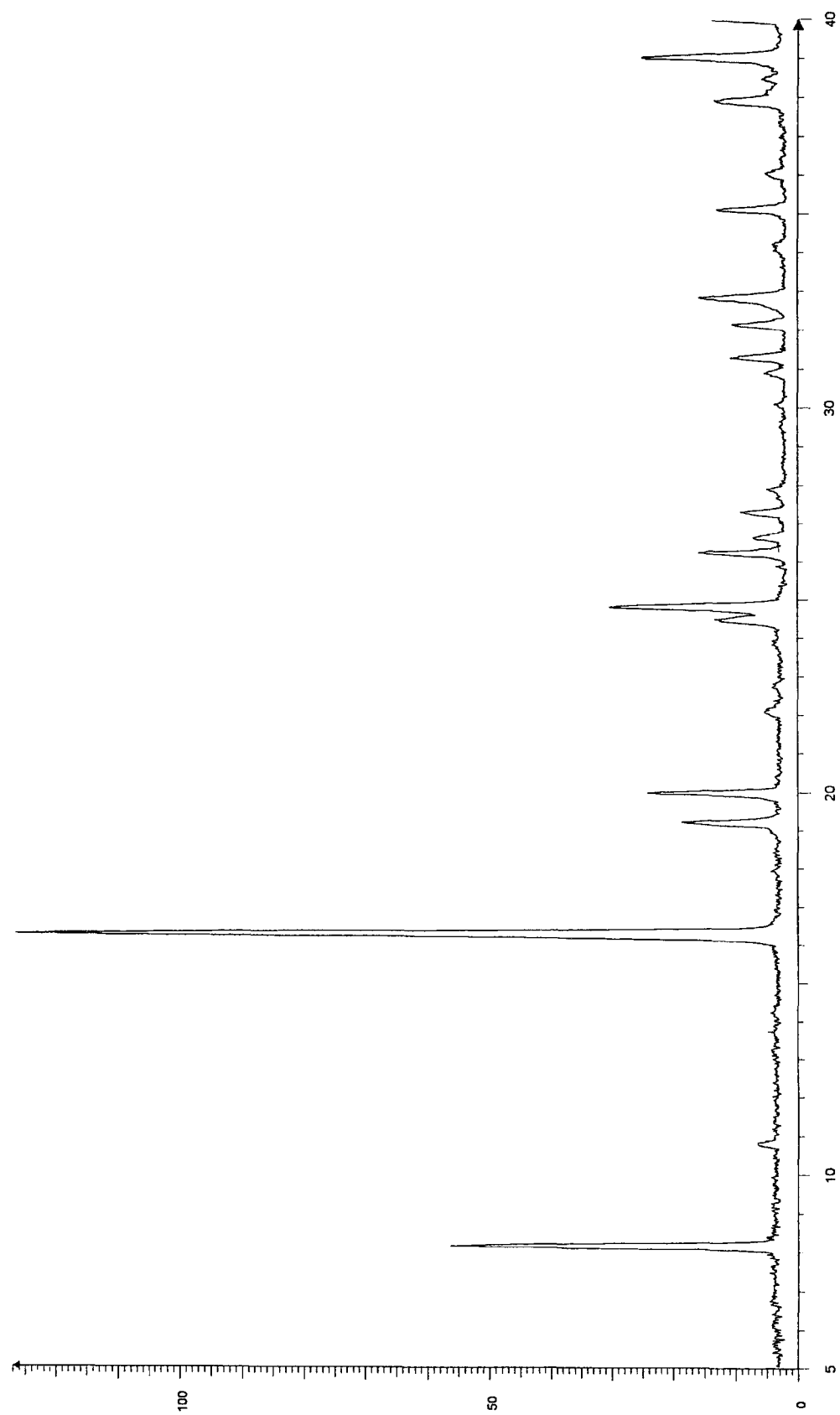
[FIG. 3] A powder X-ray diffraction pattern and a peak value thereof of the compound (13) crystal obtained in the seventh step of Example 3. An ordinate axis indicates an intensity and an abscissa axis indicates a diffraction angle (2θ, unit: degree).
Figure 4:
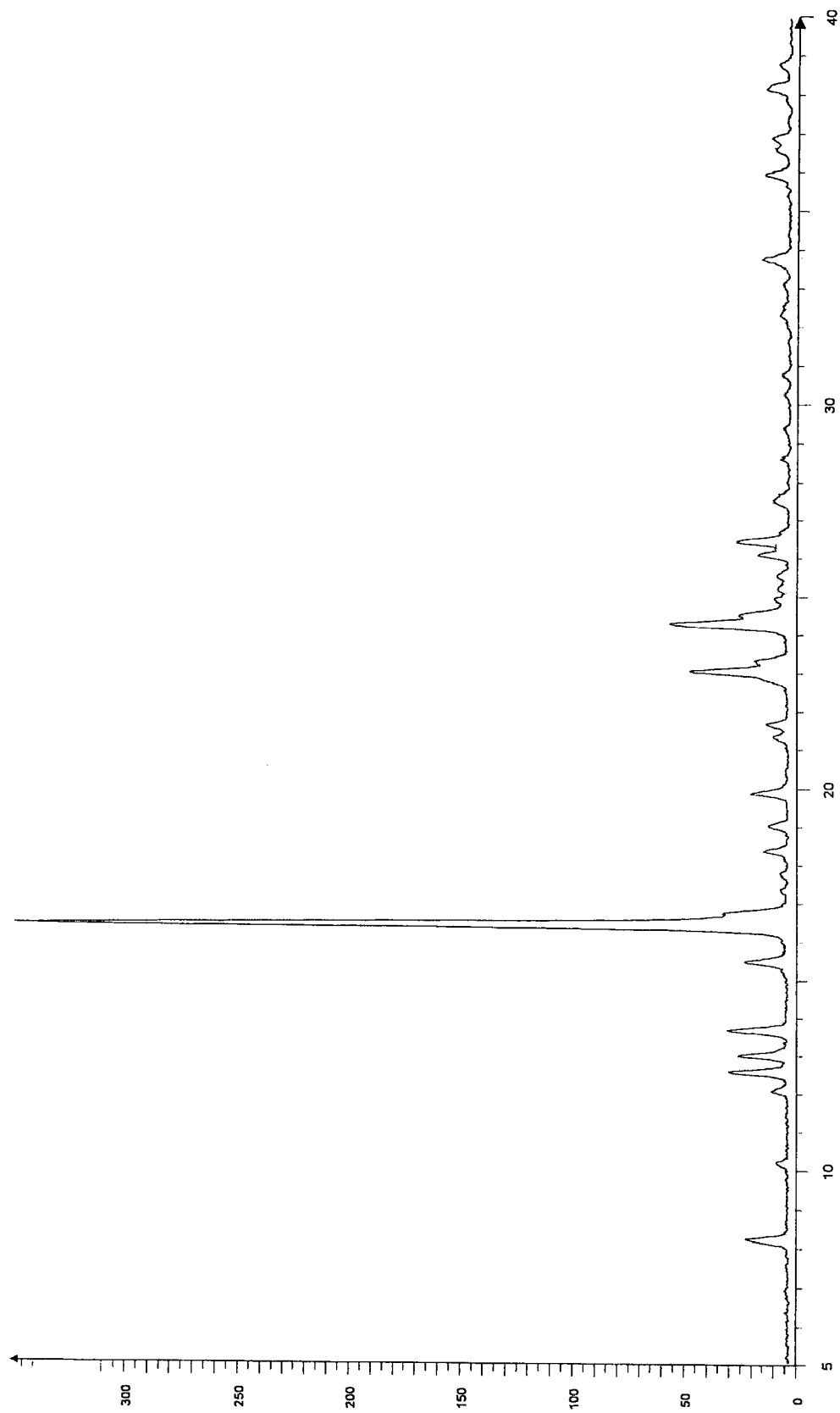
[FIG. 4] A powder X-ray diffraction pattern and a peak value thereof of the compound (20) crystal obtained in the fourth step of Example 4. An ordinate axis indicates an intensity and an abscissa axis indicates a diffraction angle (2θ, unit: degree).
Figure 5:
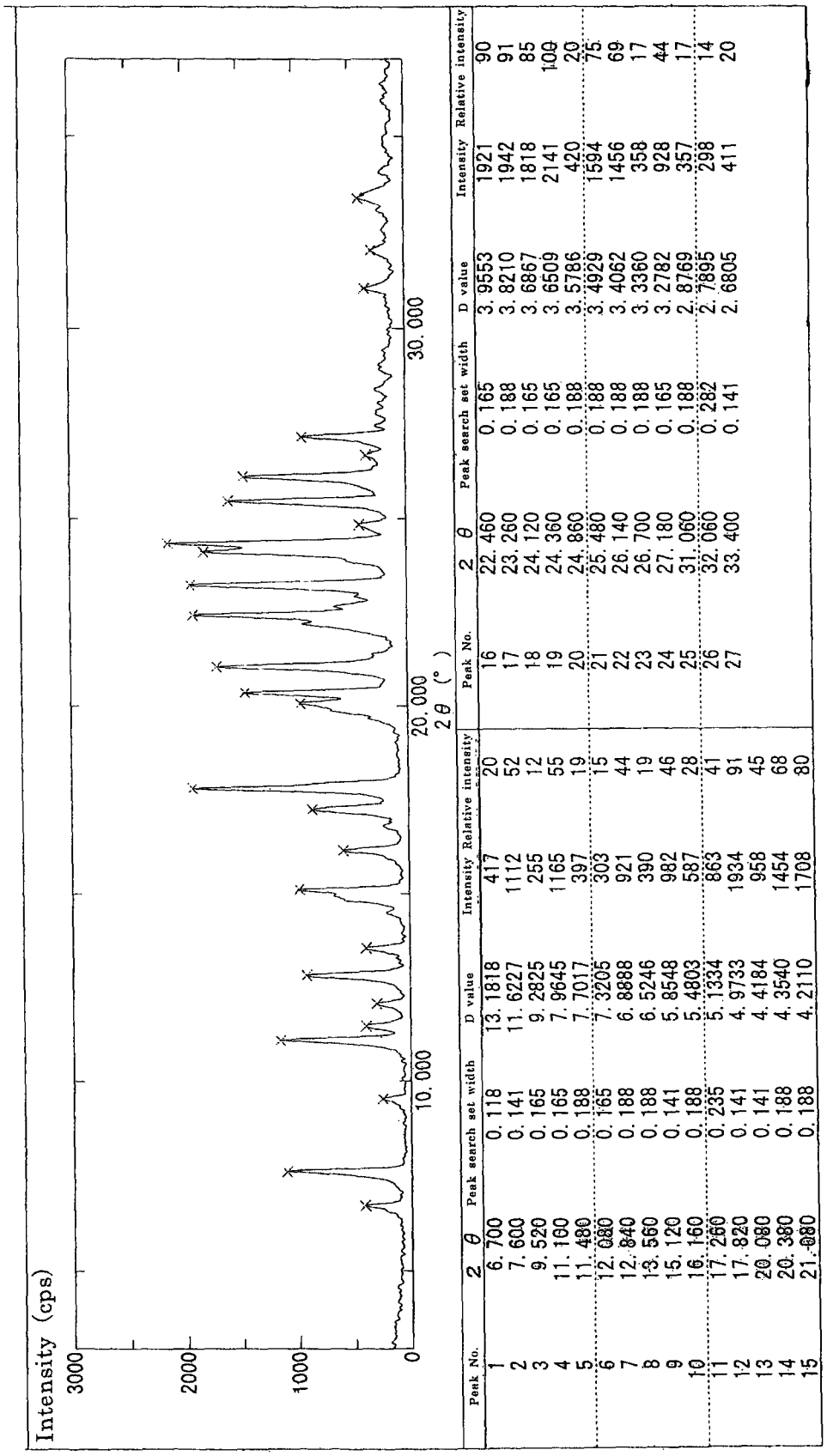
[FIG. 5] A powder X-ray diffraction pattern and a peak value thereof of the compound (C-3B) crystal obtained in the sixth step of Example 4. An ordinate axis indicates an intensity (unit: cps) and an abscissa axis indicates a diffraction angle (2θ, unit: degree).
Figure 6:
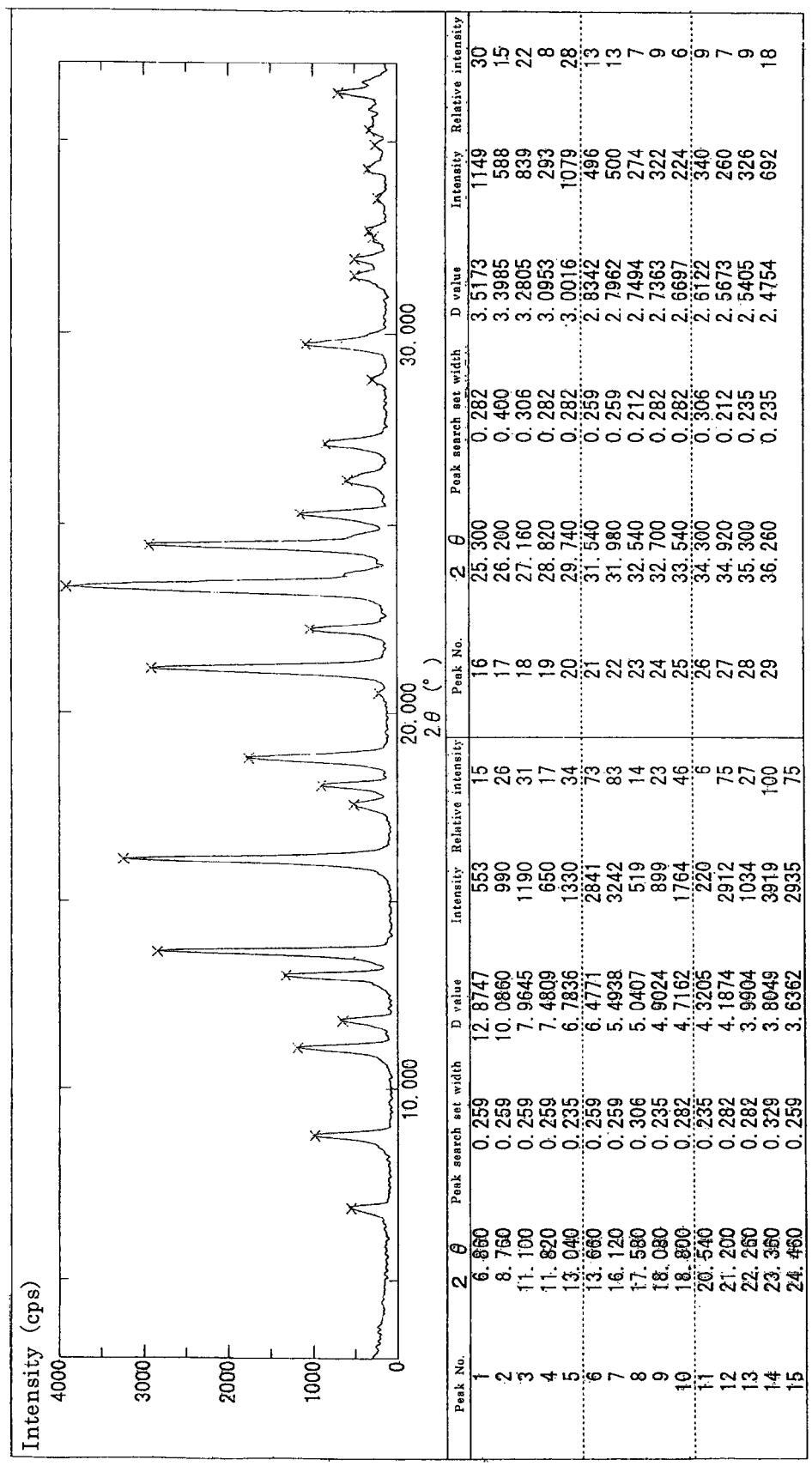
[FIG. 6] A powder X-ray diffraction pattern and a peak value thereof of the compound (C-9B) crystal obtained in the sixth step of Example 5. An ordinate axis indicates an intensity (unit: cps) and an abscissa axis indicates a diffraction angle (2θ, unit: degree).

The invention claimed is:

1. A crystal of (S)-(E)-3-(2,6-dichloro-4-{4-[3-(1-hexyloxyethyl)-2-methyloxyphenyl]thiazol-2-ylcarbamoyl}phenyl)-2-methylacrylic acid characterized by an X-ray powder diffraction pattern comprising peaks located at 17.8 degree, 21.1 degree, 22.5 degree, 23.3 degree, 24.1 degree, and 24.4 degree two-theta angles.

2. A pharmaceutical composition comprising, as an active ingredient, the crystal as defined in claim 1.

3. The pharmaceutical composition according to claim 2, comprising the active ingredient in an amount effective as a thrombopoietin receptor agonist.

4. The pharmaceutical composition according to claim 2, comprising the active ingredient in an amount effective as the platelet production regulating agent.

* * * * *